(12) United States Patent
Abramson

(10) Patent No.: US 6,355,416 B1
(45) Date of Patent: Mar. 12, 2002

(54) ASSAY FOR THE MEASUREMENT OF DNA SYNTHESIS RATES

(75) Inventor: Fred P. Abramson, Washington, DC (US)

(73) Assignee: The George Washington University, Washington, DC (US)

( * ) Notice: Subject to any disclaimer, the term of this patent is extended or adjusted under 35 U.S.C. 154(b) by 0 days.

(21) Appl. No.: 09/023,481

(22) Filed: Feb. 13, 1998

Related U.S. Application Data

(60) Provisional application No. 60/039,729, filed on Feb. 14, 1997.

(51) Int. Cl.[7] .......................... C12Q 1/68; A01N 37/18; A01N 43/04
(52) U.S. Cl. .................. 435/6; 514/2; 514/44
(58) Field of Search .............. 435/6; 514/2, 44

(56) References Cited

U.S. PATENT DOCUMENTS

| | | | |
|---|---|---|---|
| 5,338,686 A | * | 8/1994 | Hellerstein .................. 436/173 |
| 5,438,194 A | * | 8/1995 | Koudijs et al. ............. 250/288 |
| 5,910,403 A | | 6/1999 | Hellerstein ..................... 435/4 |
| 6,010,846 A | | 1/2000 | Hellerstein ..................... 435/4 |

OTHER PUBLICATIONS

Reddy et al., Analytical Biochemistry, vol. 220, pp. 200–207, 1994.*

Hellerstein et al., American Journal of Physiology, vol. 263, pp. E988–E1001, 1992.*

Crain, Methods in Enzymology, vol. 193, pp. 782–790, 1990.*

* cited by examiner

Primary Examiner—Ardin H. Marschel
(74) Attorney, Agent, or Firm—Antonelli, Terry, Stout & Kraus, LLP

(57) ABSTRACT

Use of nonradioactive tracer technology used to measure DNA synthesis rates. DNA synthesis is determined by administering one or more stable isotope labelled precursors to one or more of DNA molecules and the amount of the stable isotope label in the DNA that is extracted from cells that are of interest is measured.

18 Claims, 12 Drawing Sheets

FIG. 4
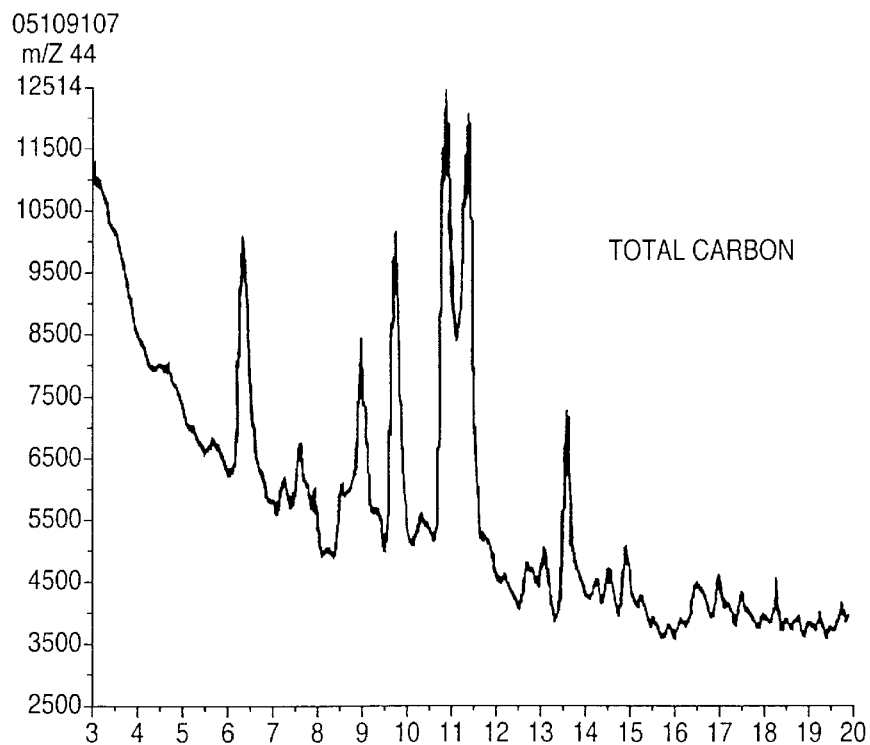
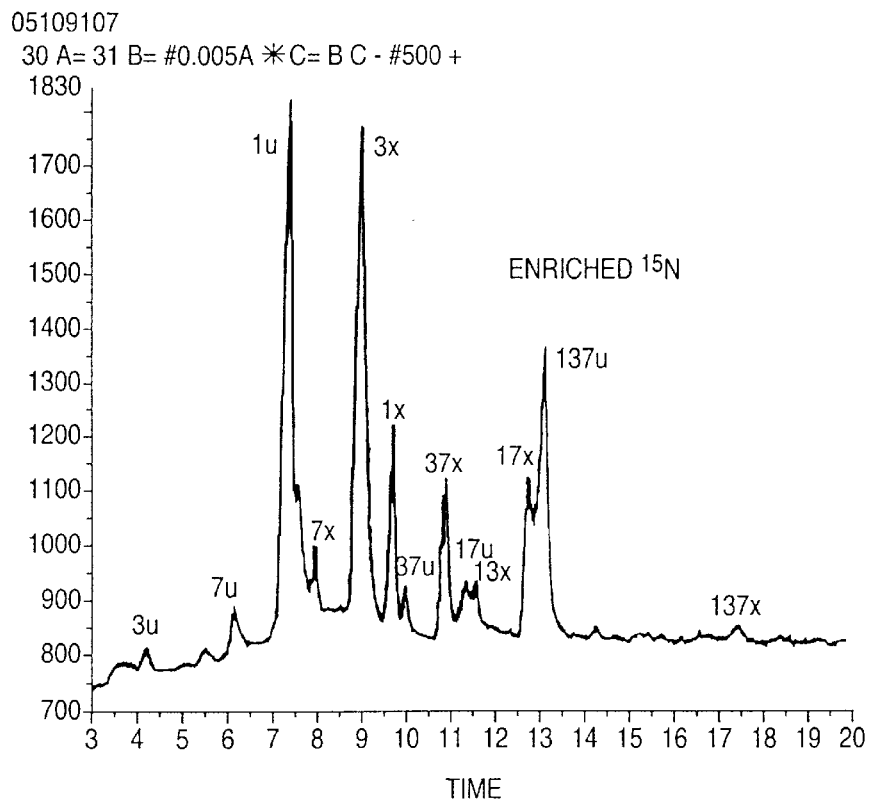
TIME

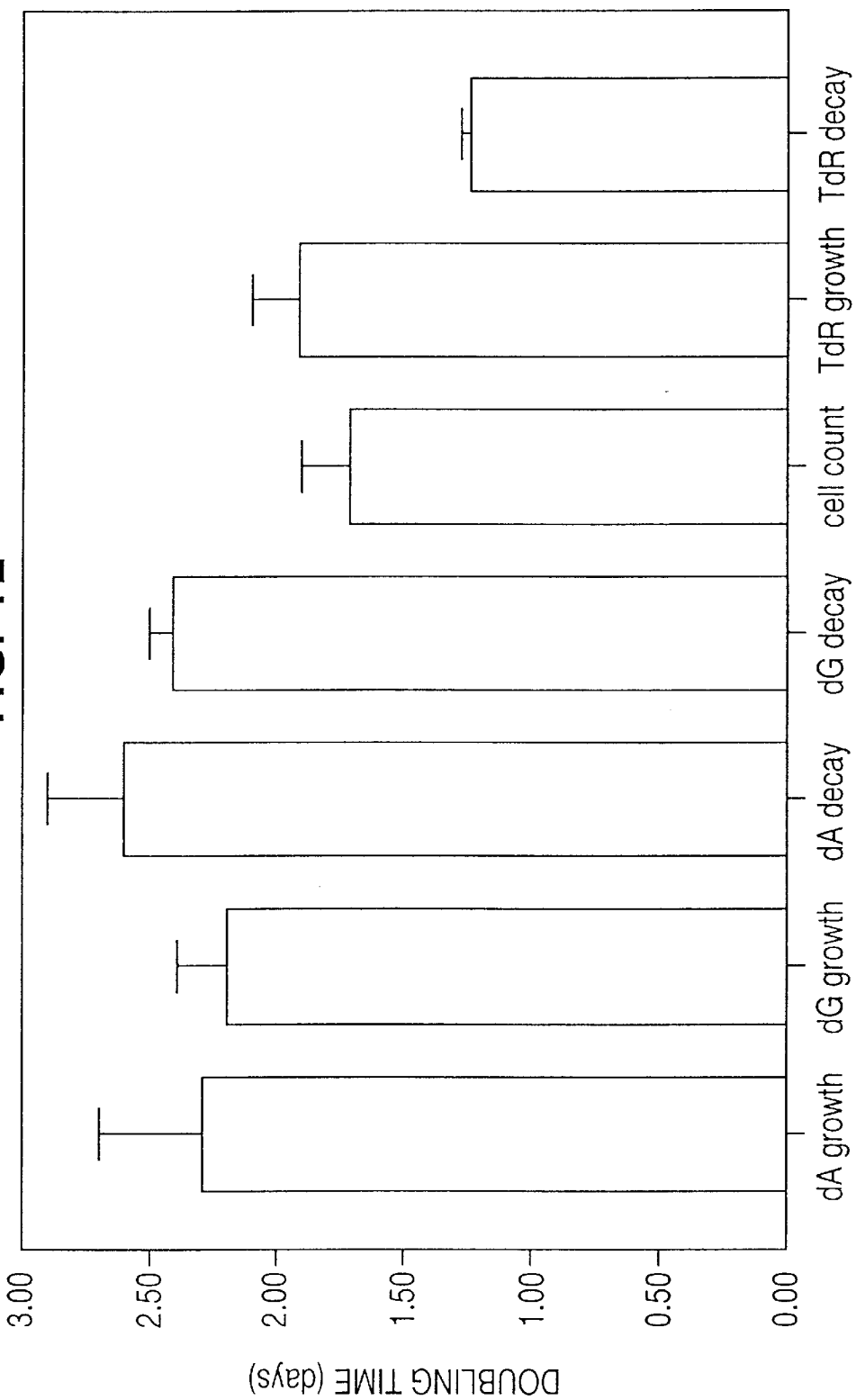

ASSAY FOR THE MEASUREMENT OF DNA SYNTHESIS RATES

CROSS-REFERENCE TO RELATED APPLICATION

This application is a continuation-in-part of provisional application Serial No. 60/039,729, filed on Feb. 14, 1997.

TECHNICAL FIELD

The invention relates to the use of nonradioactive tracer technology used to measure DNA synthesis rates. DNA synthesis is determined by administering one or more stable isotope labelled precursors to one or more of DNA substituents and the amount of the stable isotope label in the DNA that is extracted from cells that are of interest is measured.

BACKGROUND ART

The chemical reaction interface for mass spectrometry (CRIMS) was first developed by Markey and Abramson in 1982 as a way of utilizing the mass spectrometer as an element (carbon) and isotope (14C) selective detector for gas chromatography. Chace and Abramson further developed the technique to encompass a range of stable isotopes and were the first to show the application of this technique to drug metabolism. The principle of CRIMS is for the chromatographic effluent to flow into a microwave-powered reaction cell where the molecular species are broken down to elements. The continuous addition of a reactant gas to the microwave-induced plasma results in the formation of simple gaseous reaction products that are characteristic of the elements contained in the original molecule. Conventional electron ionization mass spectrometry is then used to detect elements or isotopes in these reaction products. Chemical Reaction Interface/Mass Spectrometry {CRIMS} has evolved from a concept into a selective, sensitive, and versatile technique by which targeted isotopes or elements can be monitored in studies of metabolism. CRIMS parallels the use of radioisotopes in that each technique monitors for its tracers independent from the chemical structures in which the targeted species exist. Using CRIMS, intact analyses are decomposed to their elemental species in a high temperature electronic plasma and interact with atoms of a reactant gas to form a set of new, small polyatomic species that are detected by a conventional mass spectrometer. The presence of a given polyatomic species signifies the presence of a particular element, the abundance of that species quantifies it, and the isotopic signature of that species can differentiate it from endogenous materials. By subtracting the known natural abundance of the stable isotope that is used as a tracer, a chromatogram showing only enriched species can be produced. CRIMS has been interfaced with gas and liquid chromatography, and a number of applications have been carried out.

Some isotope metabolic assays are known. For example, U.S. Pat. No. 4,182,656 discloses a method for detecting the presence of biologically active agents, utilizing a $^{13}C$-labeled substrate. The method uses $^{13}C$-labeled glucose, allows fermentation to take place and then measures the proportions of $^{13}C$ and $^{12}CO_2$ in a culture gas to ascertain whether there has been increase in the ratio of the $^{13}C^{16}O_2$ indicative of the presence of a biological active agent. Col. 10, line 45 indicates that the gas is run through a mass spectrum to determine the reference value for the ratio of $CO_2$.

U.S. Pat. No. 4,830,010, discloses methods for the diagnosis of gastrointestinal disorders. The method involves using amounts of isotope-labeled urea. The urea is labeled with one or more stable isotopes. The individual's breath is tested for the presence of isotope-labeled carbon dioxide or isotope-labeled ammonia which are hydrolysis products of campylobacter pyloridis. The gas sample is tested by mass spectroscopy.

U.S. Pat. No. 5,559,038 discloses a method for quantifying the amounts of oxidized sulfhydryl amino acids particularly cysteine sulfinic acid and cysteic acid in biological samples. The oxidized sulfhydryl amino acids are measured by gas chromatography/mass spectrometry after derivatization, using stable isotope internal standards. Deviation from normal levels indicates neuropsychiatric disorders.

Chemical Abstracts, Vol. 95, No. 7, Abstract No. 62629g discloses the "Longitudinal relaxation in a homonuclear coupled two-spin system. The case of (13C, 2H) glycine". The abstract discusses a synthesis of amino acids and peptides. *J. Magn. Reson*, 1981, Vol 42.

Chemical Abstracts, Vol. 90, No. 17, Abstract No. 135950p discloses a "Study of the effects of truncal subdiaphragmatic vagotomy and pyloroplasty on the nitrogen balance in bionomic gastric surgery in rats using the stable isotope-labelled amino acid 15N-glycine.

Chemical Abstracts, Vol. 89, No. 17, Abstract No. 147218y discloses the synthesis of cyclic peptides from glycine partially labeled with deuterium and/or carbon-13 and two pairs of proline.

Chemical Abstracts, Vol. 111, No. 13, Abstract No. 111948v discloses stable isotope dilution analysis of n-hexanoylglycine, 3-phenylpropionylglycine and suberylglycine in human urine using chemical ionization gas chromatography/mass spectrometry selected ion monitoring. *Biomed. Environ. Mass Spectrom*, 1989 VOLUME: 18 NUMBER: 7, p 471–7.

Chemical Abstracts, Vol. 111, No. 11, Abstract No. 94305p discloses the "Measurement of apolipoprotein B synthesis in perfused rat liver using stable isotopes such as 15N hippurate as a measurement of the intracellular 15N glycine precursor enrichment". The isotopes are used in measurement of ribonucleic acids, and are glycine specific. See *J. Lipid. Res*., Vol. 30, No. 6 (1989) p. 841–6.

Chemical Abstracts, Vol. 87, No. 1, Abstract No. 1970z discloses "A stable isotope method for measurement of thymidine incorporation in DNA. The abstract discloses the isotope is a cancer therapy cell growth stable isotope. Heck, Henry d'A.; McReynolds, James H.; Anbar, Michael; *Cell tissue Kinet*. 1977, Vol 10, NUMBER: 2, p. 111–19. Heck et al. use a stable isotope labeled precursor to DNA and measuring the increased DNA labeling. They did not use any de novo precursors, such as the glycine. They do not do any separations on-line. They separate each nucleic acid with thin-layer chromatography and take each purified spot for MS analysis.

Song and Abramson, Nitrogen Trifluoride: A New Reactant gas in chemical reaction interface mass spectrometry for detection of phosphorus, Deuterium, Chlorine and Sulfur. *J. Am. Soc. Mass Spectrom*., No. 6, 1995, pp. 421–427. This publication discloses generally, that chemical reaction interface mass spectrometry (CRIMS) may be used for studying metabolism without the use of radioactive labels.

Slatkin et al., Stable Isotopes, Proceedings of the Third International conference. A Postmortem study of stable carbon Isotope ratios in human Cerebellar DNA: Preliminary Results. This study showed that the stable carbon isotope ratios in human cerebellar DNA show different levels in Europeans and Americans/Canadians. DNA was isolated combusted, and purified $CO_2$ on a gas chromatograph, and measured with a mass spectrometer. This work did not attempt to alter the isotope ratio of DNA by giving a labeled precursor and were examining how different diets in different cultures lead to different $^{13}C$ ratios in subjects' DNA. Similar measurements have been made for other parts of the body, e.g., proteins, egg shell carbonate, etc.

Berthold et al., Evidence for incorporation of intact dietary pyrimidine (but not purine) nucleosides into hepatic RNA, Proc. Nat. Acad. Sci., Vol 92, page 10123–10127. This publication reports the growth of spirulina algae in $^{13}C$ labelled environment. The spirulina algae is fed to mice. Hepatic analysis of these animals showed large quantities of dietary pyrimidines are incorporated into hepatic nucleic acids. Almost no labelled purine nucleosides are incorporated into hepatic ribonucleic acids (RNA). Testing was performed using gas chromatography/mass spectrometry.

Strong et al., J. Biolog. Chem., Vol. 260 No. 7, Apr. 10, 1985, pp. 4276–4281. A Novel Approach to the Analysis of Mass Spectrally Assayed Isotope-labelling Experiments. This publication discloses the use of $^{15}NH_4Cl$ and L-glutamine as precursors in the study of de novo pyrimidine (uracil) biosynthetic pathways. Quantitation of the labelled uracil was performed with a mass spectrometer. The authors were not examining DNA synthesis rates.

Macallan, et al present a different approach to measuring DNA synthesis rates with stable isotopes and mass spectrometry. Macallan, et al has shown that DNA synthesis rates can be measured with a stable isotopic precursor and mass spectrometry. Their method differs markedly from the inventor's method in a number of substantive ways. The precursor, $[6,6-_2H_2]$-glucose, is not incorporated into the nucleic acid base as does the present method, but labels the deoxyribose component. As such, every component of DNA will be labeled, thus failing to provide any internal standards. Furthermore, glucose is a nutrient with high blood concentrations that requires at least 100-fold more labeled material to achieve a comparable isotopic enrichment compared to glycine or any of the nucleosides or bases that comprise DNA. A second major difference is that the method of Macallan uses gas chromatography (GC) to separate and introduce the DNA components rather than the high performance liquid chromatography (HPLC) that the inventor has used. With GC the nucleosides have to be chemically derivatized, a process that contributes to a 16% interference at the mass where the labeled DNA-derived materials are detected. With the preferred use of HPLC, this interference is reduced because no derivatization is required. A third difference is that Macallan examines the intact derivatized nucleosides using mass spectrometry while the inventor has used CRIMS. By doing so, the invention has only a 1% interference at the mass where the labeled DNA-derived materials are detected. Finally, by using an IRMS rather than the conventional MS approach of Macallan, the inventor is able to determine perhaps 1000-fold lower isotopic enrichments, thus making that approach much more practical. Macallan examined cells in culture, intestinal epithelium, thymus, and liver cells from rats, and granulocytes from humans.

The current state of the art uses a radiolabelled tritiated thymidine for metabolic diagnostic testing. Thus, there is a need in the art for sensitive DNA synthesis testing and diagnostic testing without the use of a radiolabel. The present invention overcomes deficiencies in the prior art and provides for a sensitive assay to provide measurement of DNA synthesis without the use of a radioactive label.

DISCLOSURE OF THE INVENTION

In a preferred embodiment the invention provides an assay for detection of DNA synthesis comprising the steps of
(a) adding a stable isotope labelled DNA precursor to a replicating DNA sample;
(b) isolating a portion of said replicating DNA sample comprising said stable isotope; and
(c) measuring the enrichment of stable isotope label in newly synthesized DNA with an isotope ratio mass spectrometer, wherein the stable isotope labelled precursor to DNA is incorporated via de novo purine or pyrimidine biosynthesis or by biochemical metabolic salvage pathways and is synthesized into a new strand of DNA.

In an alternative embodiment the invention provides a method of measuring the enrichment of stable isotopes of hydrogen, carbon, oxygen and nitrogen in replicating DNA comprising the steps of:
(a) adding a stable isotope labelled DNA precursor to a replicating DNA sample;
(b) isolating a portion of said replicating DNA sample comprising said stable isotope; and
(c) measuring the enrichment of stable isotope label in newly synthesized DNA with a chemical reaction interface mass spectrometer, wherein the stable isotope labelled precursor to DNA is incorporated via de novo purine or pyrimidine biosynthesis or by biochemical metabolic salvage pathways and is synthesized into a new strand of DNA.

In still another embodiment the invention provides an assay for detection of DNA synthesis comprising the steps of
(a) adding a stable isotope labelled DNA precursor to a replicating DNA sample;
(b) isolating or purifying a portion of said replicating DNA sample comprising said stable isotope;
(c) combusting the DNA of step (b) to produce a stable isotope labelled combustion product, (e.g. $CO_2$) on which an enrichment measurement is made;
(d) measuring the enrichment of stable isotope label in newly synthesized DNA with a mass spectrometer, wherein the stable isotope labelled precursor to DNA is incorporated via de novo purine or pyrimidine biosynthesis or by biochemical metabolic salvage pathways and is synthesized into a new strand of DNA.

Advantageously the invention provides an assay for detection of DNA synthesis comprising the steps of
(a) adding a stable isotope labelled precursor to a replicating DNA sample;
(b) isolating or purifying a portion of said replicating DNA sample comprising said stable isotope;
(c) optionally degrading the DNA of step (b);
(d) analyzing the DNA obtained in steps (b) or (c) by chromatography; and
(e) measuring the enrichment of stable isotope label in newly synthesized DNA with a mass spectrometer, wherein the stable isotope labelled precursor to DNA is incorporated via de novo purine or pyrimidine biosynthesis or by biochemical metabolic salvage pathways and is synthesized into a new strand of DNA.

Still another embodiment provides an assay for detection of DNA synthesis comprising the steps of
(a) adding a stable isotope labelled DNA precursor to DNA, wherein said labelled DNA precursor does not label all four DNA bases;

(b) isolating or purifying a portion of said replicating DNA sample comprising said stable isotope;

(c) degrading the DNA of step (b);

(d) analyzing the degraded DNA by high performance liquid chromatography, wherein said chromatography allows the non-labeled DNA components to serve as an internal standard for the labeled DNA; and (e) measuring the amount of stable isotope label in the DNA by chemical reaction interface mass spectroscopy (CRIMS); wherein the stable isotope labelled precursor to DNA is incorporated via de novo purine or pyrimidine biosynthesis or by biochemical metabolic salvage pathways and is synthesized into a new strand of DNA.

An application of the assay of the invention provides a method of measuring the effectiveness of chemotherapeutic drugs comprising (a) administering a stable isotope labelled precursor to DNA to a patient who has received chemotherapy, wherein said labelled precursor does not label all four DNA bases;

(b) obtaining a replicating DNA sample from said patient who has received chemotherapy;

(c) isolating or purifying a portion of said replicating DNA sample comprising said stable isotope;

(d) degrading the DNA of step (c);

(e) analyzing the degraded DNA by chromatography (preferably high performance liquid chromatography), wherein said chromatography allows the non-labeled DNA components to serve as an internal standard for the labeled DNA; and (f) measuring the amount of stable isotope label in the DNA by mass spectroscopy;

wherein the stable isotope labelled precursor to DNA is incorporated via de novo purine or pyrimidine biosynthesis or by biochemical metabolic salvage pathways and is synthesized into a new strand of DNA.

The above and other objects of the invention will become readily apparent to those of skill in the relevant art from the following detailed description and figures, wherein only the preferred embodiments of the invention are shown and described, simply by way of illustration of the best mode of carrying out the invention. As is readily recognized the invention is capable of modifications within the skill of the relevant art without departing from the spirit and scope of the invention.

BRIEF DESCRIPTION OF DRAWINGS

FIG. 4. Metabolic pattern of caffeine determined by enriched $^{15}N$ and HPLC/CRI-MS. Legend: X=xanthine, U=uric acid, numbers refer to positions of the methyl groups. Caffeine=137X.

FIG. 12 shows a summary of HEP G2 doubling times from each of the seven types of experiments carried out. Each bar represents the fit based on an exponentially-growing cell population and the standard error of the parameter estimate from the appropriate nonlinear regression.

DESCRIPTION OF THE INVENTION

Figure 1:
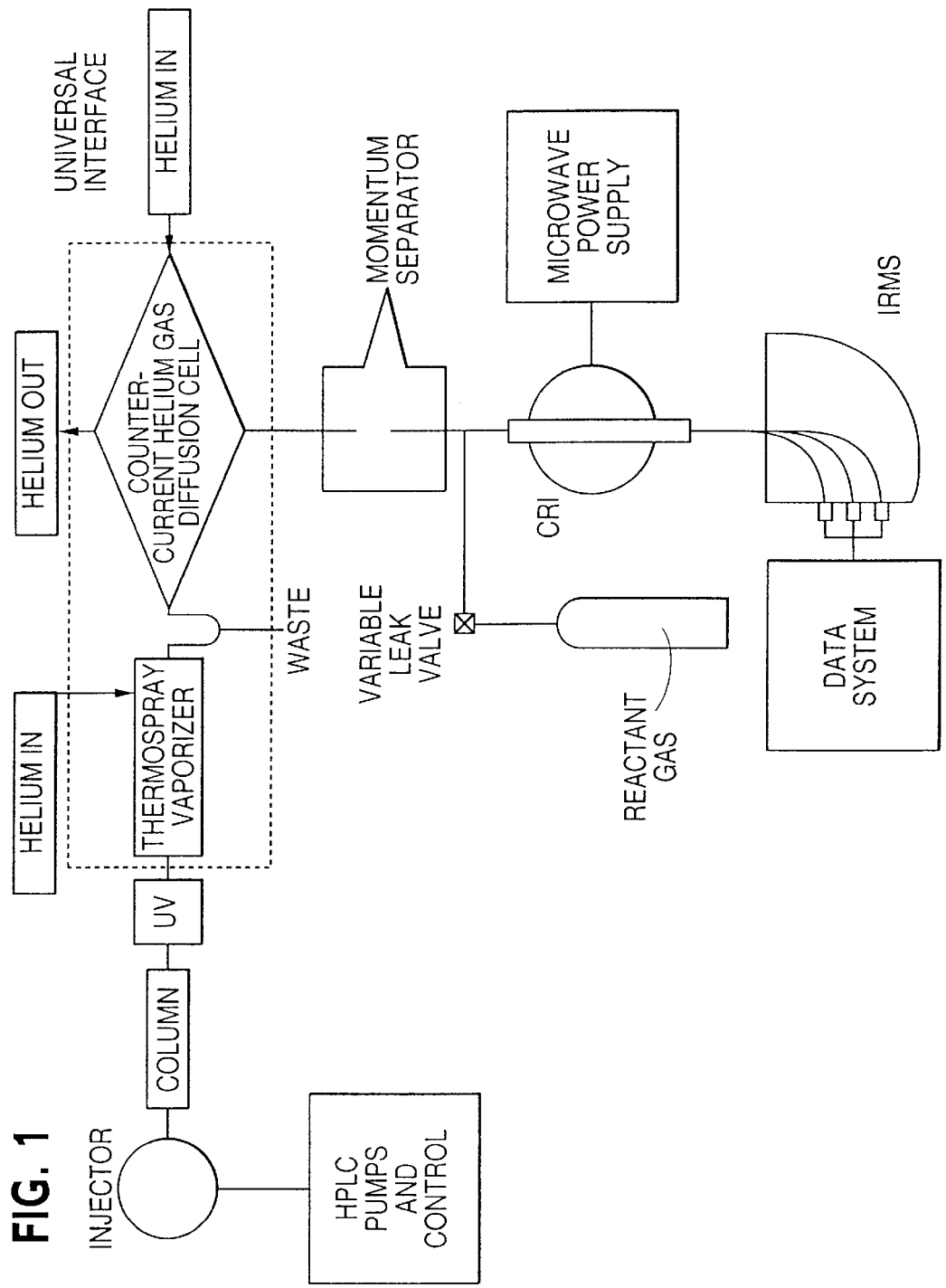
FIG. 1 shows a scheme for the chromatography/mass spectroscopy apparatus which is used in a preferred embodiment of the invention.

Thus the present invention provides for an assay for detection of DNA synthesis comprising the steps of (a) adding a stable isotope labelled DNA precursor to a replicating DNA sample;

(b) isolating or purifying a portion of said replicating DNA sample comprising said stable isotope;

(c) combusting the DNA of step (b) to produce a stable isotope labelled combustion product, (e.g. $CO_2$) on which an enrichment measurement is made;

(d) measuring the enrichment of stable isotope label in newly synthesized DNA with a mass spectrometer, wherein the stable isotope labelled precursor to DNA is incorporated via de novo purine or pyrimidine biosynthesis or by biochemical metabolic salvage pathways and is synthesized into a new strand of DNA. In the assay the stable isotope may be a stable isotope of hydrogen, oxygen, carbon or nitrogen.

In a preferred embodiment the labelled DNA precursor is selected from the group consisting of glycine, adenosine, cytosine, guanine and thymine. Any precursor to a de novo DNA metabolic pathway, or DNA production salvage pathway may be used in the assay of the invention.

In an alternative embodiment the type of chromatography is high performance liquid chromatography, gas chromatography or capillary electrophoresis. In a most preferred embodiment the chromatography apparatus is linked to the mass spectrometer.

Any spectrometer may be used in the assay of the invention. A chemical reaction interface mass spectrometer or an isotope ratio mass spectrometer provide exceptional measurement results.

The assay of the invention may use nonradioactive tracer technology used to measure DNA synthesis rates. DNA synthesis is determined by administering one or more stable isotope labelled precursors to one or more of DNA substituents and the amount of the stable isotope label in the DNA that is extracted from cells that are of interest is measured. To perform such an assay, a suitable stable-isotope labeled precursor to a portion of DNA (such as 1-$^{13}C$-glycine or $^{15}$N-labeled thymidine) is given in one or more doses so that the DNA being synthesized will contain the stable isotope. For example an atom of $^{13}$C in one position of glycine is incorporated via de novo purine biosynthesis and subsequently synthesized into a new strand of DNA, a labeled base would measure salvage pathways. The measurement of the stable isotope labeled DNA involves the use of mass spectrometry (MS). This technique can measure enrichment of stable isotopes of hydrogen, carbon, oxygen and nitrogen depending on the particular type of mass spectroscopy (MS) used, as little as one part in a million of excess isotope might be detected.

In one embodiment of the assay of the invention the labelled DNA precursor is 1-$^{13}$C glycine and only $C_5$ of the synthesized DNA purines are labelled and not pyrimidines. Alternatively the DNA precursor may be any of cytosine, adenosine, thymine, guanine and the non-labelled base or bases in the chromatography results may be used as a baseline against which the enrichment in guanosine or adenosine in the synthesized DNA is measured.

DNA is not now capable of being accurately measured by MS, but there are a variety of methods by which DNA can be made amenable to this measurement. The DNA may be purified and/or combusted, thus producing $CO_2$ on which the enrichment measurement is made. Alternatively DNA can be completely degraded, for example into nucleotides, nucleosides, or the bases and then analyzed by chromatographic introduction.

Recently, high performance liquid chromotomography (HPLC) columns have appeared that are capable of eluting DNA fragments containing thousands of base pairs. A restriction enzyme digestion is used to degrade genomic DNA down to a level which can be subjected to chromatography. Furthermore, any of the above methods can be used to measure the rate at which this DNA label turns over.

After the stable isotope precursor to DNA disappears, the labeled DNA will decrease in its abundance with some proportionality to the rate at which DNA is now synthesized or repaired. Any treatment that altered cellular division, or otherwise altered DNA synthesis or repair, would be manifest as an alteration in the rate at which the labeled DNA disappeared. Cancer, aging and many other diseases that affect proliferation could be investigated. A wide range of applications for using this type of analysis are available.

Diseased states, or treatments for disease states, that affected cellular growth could be measured in this manner. DNA repair rate might be measured by this method. Being nonradioactive, the approach could be used in vivo, to monitor or diagnose human diseases and their treatments without fear of radiation hazards. The assay can be used to measure the effect of chemotherapeutic drugs on DNA synthesis.

The invention preferably uses an HPLC and a continuous flow isotope ratio mass spectrometer. The component pieces are: 1. a high performance liquid chromatograph (HPLC); 2. a Vestec Universal HPLC/MS interface; 3. a chemical reaction interface (CRI); and 4. an isotope ratio mass spectrometer system (IRMS).

The CRIMS provides an extensive range of CRI-MS applications using capillary gas chromatography coupled to conventional mass spectrometers; and the recent development of an interface to the CRI for HPLC makes this approach possible. The unique chemistry of the CRI improves $^{15}$N determinations compared with classical combustion methods. This type of instrument offers researchers who use isotopes and IRMS an expanded range of target molecules including intact biological polymers. Compared to HPLC/conventional MS approaches, $^{13}$C and $^{15}$N are selectively detected at greatly reduced isotopic abundance. In addition, intact biological macromolecules can be analyzed directly by the CRI-IRMS for isotopic quantitation. This greatly improves analyses in biological systems where either $^{14}$C is a tracer or where the tedious sequence of hydrolysis followed by chromatographic separation and MS analysis of selected monomers is required.

THE CHEMICAL REACTION INTERFACE

A preferred apparatus for use in the assay of the invention uses a microwave-powered chemical reaction interface (CRI). This device decomposes analytes and reformulates them into small molecules whose spectra permit selective detection of stable isotopes in organic molecules in a manner that is independent of the structure of the original analyte molecule; a characteristic otherwise requiring radioactivity. Most of the use of the CRI involve chromatographic separations and detection with a single-collector, rapidly scanning mass spectrometer (MS).

AN ISOTOPE-RATIO MASS SPECTROMETER

The multiple collector arrangement of an isotoperatio mass spectrometer (IRMS) provides the ability to detect enrichments orders of magnitude below what can be achieved with conventional mass spectrometers.

A universal interface (UI) is capable of essentially complete removal of HPLC solvent from the analytical sample stream. It uniquely enables HPLC introduction to the CRI, as even 1/100,000 retention of the solvent could overwhelm its chemistry. This elevates the $CO_2$ baseline in the IRMS. In collaboration with Vestec Inc., the inventor has produced a CRI-MS instrument that separates mixtures with high performance liquid chromatography rather than gas chromatography as has been the previous introduction method.

This apparatus provides a new analytical concept, HPLC/CRI-IRMS for diagnostic assays, particularly those of biological and pharmacological importance. The detection of stable isotopes in compounds as simple as urea, and amino acids, and as complicated as DNA may be performed on this apparatus.

The CRI provides an alternative to the combustion system that is the "standard" for IRMS instruments that use gas chromatographic introduction. The advantages of the CRI are: an essentially unlimited supply of oxidizing gas compared to the limited capacity of a CuO combustor or other chemical reactors; the detection of nitrogen as NO, thus avoiding the problems of interference between CO and $N_2$; and the ability to vary the chemistry to monitor a wider range of isotopic species, such as $^{18}$O or $^{34}$S.

The increasing use of HPLC in biological chemistry shows that an HPLC/IRMS instrument is a major advance by assisting in metabolic studies of materials that are not appropriate for GC. Beyond the ability of HPLC to introduce samples that require separation, using flow injection (i.e., post-column introduction directly into the solvent stream) of previously purified samples, a greatly widened range of materials could be provided by the CRI interface, in particular intact biological macromolecules.

The apparatus provides high precision isotopic determinations which would greatly reduce analysis time for these large molecules which now have to be degraded to monomers (or small oligomers) which then have to be further purified, separated, and analyzed before knowing how much of a particular label has been incorporated. The complication of aberrant isotopic character of carbon-based derivatization procedures that are frequently required for GC will be negated in high precision IRMS measurements with HPLC.

In general, stable isotopes are favored in human experimentation, since they are free of the risks associated with radioisotopes. Because there are no radioisotopes of nitrogen, the use of $^{15}N$ as a tracer is particularly significant. The enhanced detection limits of an IRMS compared to a conventional MS means that human and other tracer experiments will be more readily accomplished.

ISOTOPE RATIO MEASUREMENTS IN BIOLOGICAL SYSTEMS

Isotope ratio mass spectrometry in biological systems stems from the late 1930s with the pioneering work of Rittenberg. In general, a suitably prepared sample is converted off-line, frequently by combustion in a sealed tube, into small polyatomic species such as $CO_2$, $N_2$, and $H_2O$. This gas is introduced into a multicollector mass spectrometer under controlled conditions over a long period of time so that the 45/44 i.e. $[(^{13}C^{16}O_2 + ^{12}C^{17}O^{16}O)/^{12}C^{16}O_2]$ ratio is precisely determined. This approach will be referred to as "off-line combustion IRMS".

The aspect of IRMS which is particularly applicable dates from 1976. Sano et al. (S1) first described an instrument where a GC, a combustor, and an IRMS are coupled together. The next precedent is provided by Matthews and Hayes (M3). Without use of a multicollector IRMS, they obtained high precision, low abundance detection of $^{13}C$ and $^{15}N$. With this approach, they could measure 0.02 APE for $^{13}C$ from 9 nmol of methyl octanoate. Atom Percent Excess (APE) is the difference between the isotope ratio of an unknown minus the isotope ratio of a standard IR(x)–IR(std)) times 100, divided by (1+IR(x)–IR(std)).

In comparison, the technique involving off-line combustion followed by a dual inlet, dual collector IRMS measurement required 230 nmol to produce this measurement, albeit with a 5-fold better precision. Matthews and Hayes reported that this apparatus could detect 0.2 pmol excess $^{13}C$ in a sample containing 10 nmol of carbon. For nitrogen, they examined plasma amino acids and concluded that 4 pmol excess $^{15}N$ could be determined in 100 nmol of nitrogen.

In 1984, Barrie et al. (Bi) coupled a gas chromatograph and a multicollector stable isotope ratio mass spectrometer using a combustion interface much like Matthews and Hayes. In general, their results compared to dual inlet dual collector IRMS agreed within a $\delta^{13}C$ of 2, i.e., a 0.2% error. The $\delta$ (‰) notation denotes the relative difference in isotope ratio between an unknown and a standard: $\delta=[IR(x)-IR(std)]/IR(std)\cdot 1000$. The authors concluded that:

"We would expect the gas chromatography/SIRA [stable isotope ratio analyzer] technique to reduce the quantity of labelled compound required by at least a factor of 10 and to permit new studies to be undertaken where labelled compounds are only available at enrichments too low to be utilized using GC/MS/SIM [selected ion monitoring]".

There are two commercially available GC/combustion/IRMS instruments e.g. Finnegan MAT (F2, H3)) that follows this design strategy. Published data indicate that the system can obtain precision comparable to that obtained with off-line combustion IRMS analysis.

The concept of continuous flow GC/isotope ratio measurements has been clearly defined and evaluated. When the GC and combustor are coupled to a single-collector mass spectrometer which switches peaks between masses and detects with an electron multiplier, substantially better performance is realized than from straightforward selected ion recording GC/MS experiments. A single-collector or "conventional" mass spectrometer refers to any instrument that jumps, scans, or detects two masses sequentially, rather than simultaneously. In this context, most quadrupole, magnetic sector, ion trap, and time of flight mass spectrometers are single-collector. When coupled with a mass spectrometer with multiple Faraday collectors, the GC/combustor/IRMS appears to produce nearly as good a result as off-line combustion IRMS methods, but from substantially less material. Obviously, the need to obtain purified specimens and to manipulate them prior to the IRMS measurement is obviated by the in-line GC and combustor.

In one of the few pharmacological studies with IRMS, Nakagawa et al. (N1) used off-line combustion IRMS measurements on urinary and plasma $^{13}C$ and $^{15}N$ following $2\text{-}^{15}N$, $1\text{-}^{13}C$-labeled antipyrine administration to Wistar rats. They found good comparisons in total label concentrations in blood and the specific concentration of the labeled antipyrine as measured by GC/MS/selected ion monitoring. They were also able to carry out a mass balance from urine comparable to that typically done with radiolabeled drug.

One other IRMS technique is the coupling of an elemental analyzer, a GC, and an IRMS. This was first accomplished for both $^{13}C$ and $^{15}N$ in 1985 (P2). With this combination, a packed column GC separates the fixed gas combustion products $N_2$ and $CO_2$ before they flow into a dual collector IRMS. It appears to be an efficient system for preseparated or unseparated materials, but cannot be continuously coupled to another separation device (i.e. GC or HPLC) because each analysis takes several minutes.

THE BACKGROUND OF CRI-MS

Markey and Abramson (M1, M2) developed the chemical reaction interface: a microwave-powered device which completely decomposes a complex molecule to its elements in the presence of helium. The addition of a reactant gas, for example oxygen, generates stable oxidation products that reflect the elemental composition of the original analyte and are detected by a single-collector mass spectrometer. The general characteristics of this process, although greatly simplified, are illustrated in the following scheme 1.

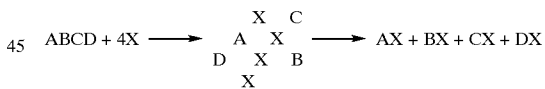

A complex molecule composed of elements represented by the letters A B C and D is mixed with an excess of reactant gas X in a stream of helium. In a CRI-MS analysis, if B is an isotope or element of interest, it can be monitored with a characteristic mass from BX with any MS. A schematic of a GC/CRI-MS apparatus is shown in FIG. 1 of Reference C1. The combination of capillary gas chromatograph and a chemical reaction interface-mass spectrometer (GC/CRI-MS) allows the analyst to selectively detect stable-isotope labeled substances as they elute. If the molecule BX has been selected to monitor a specific isotope, say at M+1, a chromatogram showing only enriched BX will be generated with Equation 1.

Enriched BX=BX at M+1–Nat. abund. of M+1 expected from BX at M. (Eq. 1). This equation removes the contribution from the naturally abundant isotopes in BX, thus leaving only the M+1 from BX that arises from the tracer. This provides the isotope-selective detection capability of CRI-MS.

The important chemistry of the CRI that applies to IRMS work is oxidation. The following reaction products are seen for elements contained in organic molecules [the masses indicate the typical range of multi-isotopic species]:

| | | |
|---|---|---|
| C | → $CO_2$ | [m/z 44, 45, 46] |
| | → CO | [m/z 28, 29, 30] |
| N | → $N_2$ | [m/z 28, 29, 30] |
| | → NO | [m/z 30, 31, 32] |
| | → $NO_2$ | [m/z 46, 47, 48] |
| H | → $H_2O$ | [m/z 18, 19, 20] |

Oxygen atoms from analyte molecules will primarily exchange with the oxygens in the reactant gas and be undetectable in the huge background. The presence of CO from carbon does not indicate that the reaction is incomplete, but indicates that, in addition to the CO+ fragment, $CO_2$ is not itself stable at the ~4000° K. temperature of a helium plasma. Introduction of pure $CO_2$ shows a substantial disproportionation to form CO+½$O_2$. The observed CO is generally of similar abundance to the $CO_2$. The CRI will not tolerate as much oxidizing material as might be required to move this equilibrium so that the vast majority of carbon appears at m/z 44. Nitrogen chemistry is even more interesting in the CRI. If $O_2$ is the reactant gas (i.e., the X in Scheme 1), the predominant species observed is $N_2$, with about 10% as much NO and 1% $NO_2$. When $SO_2$ is the reactant gas, NO is at least as abundant as $N_2$, and $NO_2$ is still about ⅒ of the NO. While both $O_2$ and $SO_2$ produce an abundance of $O_3$ in the spectrum of reactant gas products observed in the mass spectrometer, $SO_2$ also produces $SO_3$. Presumably this promotes the formation of NO at the expense of $N_2$. Another view of the relative stability of $N_2$ and $O_2$ in the plasma is that when $N_2$ is the reactant gas for the CRI, organic oxygen is observed primarily as $O_2$ and not any oxide of nitrogen. Although we have not fully evaluated it, $N_2$ as a reactant gas could be useful as a scheme for $^{17}O$ or $^{18}O$.

Work to date has firmly established that CRI-MS is a sensitive, selective, and reliable method for detecting and quantifying isotopes or elements in biological systems. Various CRI-MS experiments have successfully used urine, plasma, tissue extracts, isolated hepatocytes in culture, and cell culture media with no matrix problems.

A device as shown in FIG. 1 first desolvates a thermospray-nebulized effluent in a helium stream, then removes the residual vapor with a helium countercurrent (V1). Less than one part in $10^6$–$10^8$ of solvent are retained. Following a momentum separator (FIG. 2) to reduce the L/min flow of helium to a mL/min flow, the sample stream is characterized by an extremely "dry" array of analyte particles in He. Other than moving belts, this appears much better than other HPLC/MS interfaces. The outflow of the UI is appropriate for introduction to the CRI which normally operates with analytes carried in a 1–2 mL/min stream of He. The inventor's work to date has generated a design that effectively couples HPLC, the UI, and the CRI to both magnetic sector MS, conventional quadrupole MS and IRMS.

Figure 2:
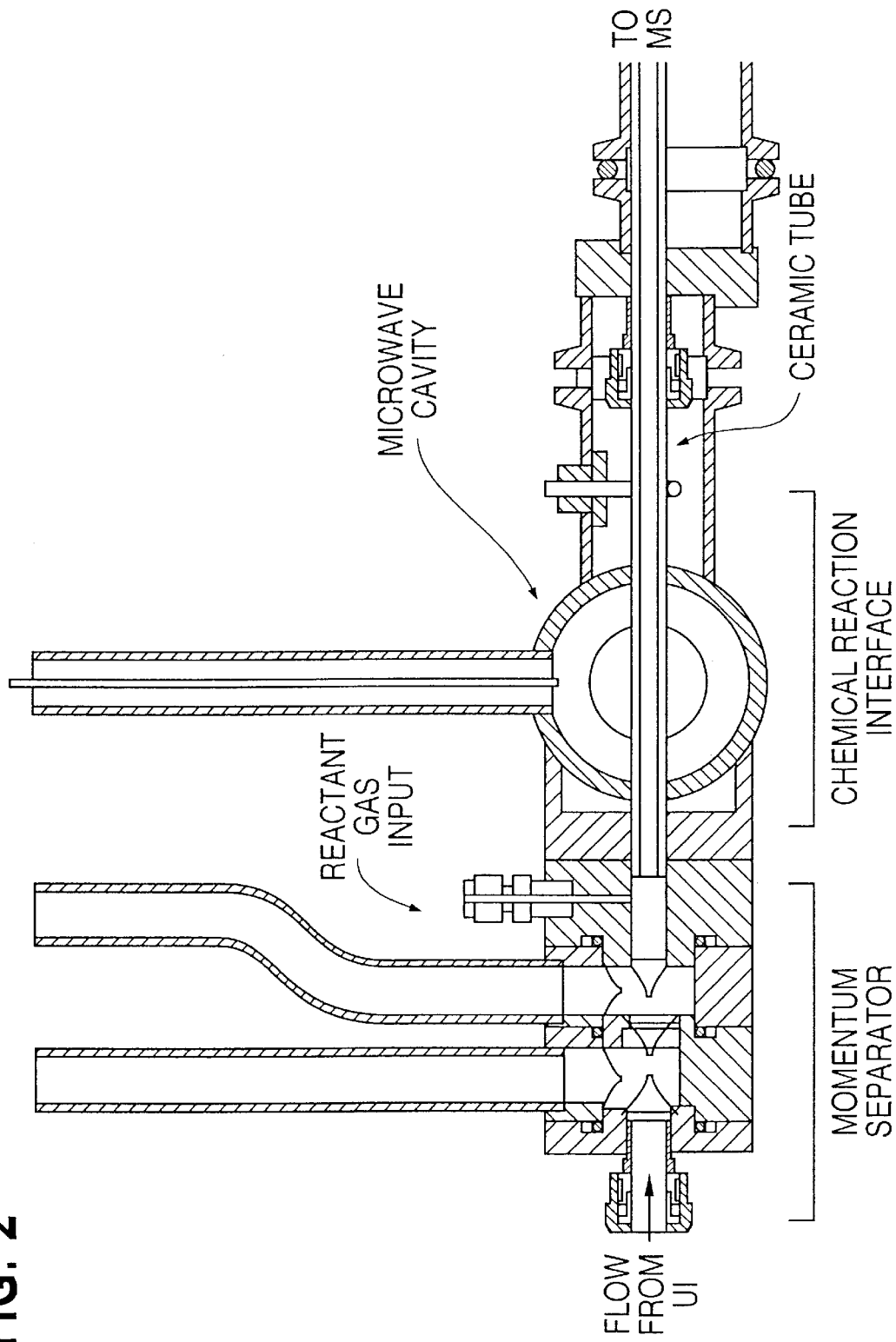
FIG. 2. Schematic of CRI-MS probe for HPLC introduction with Vestec Universal Interface.
Figure 3:
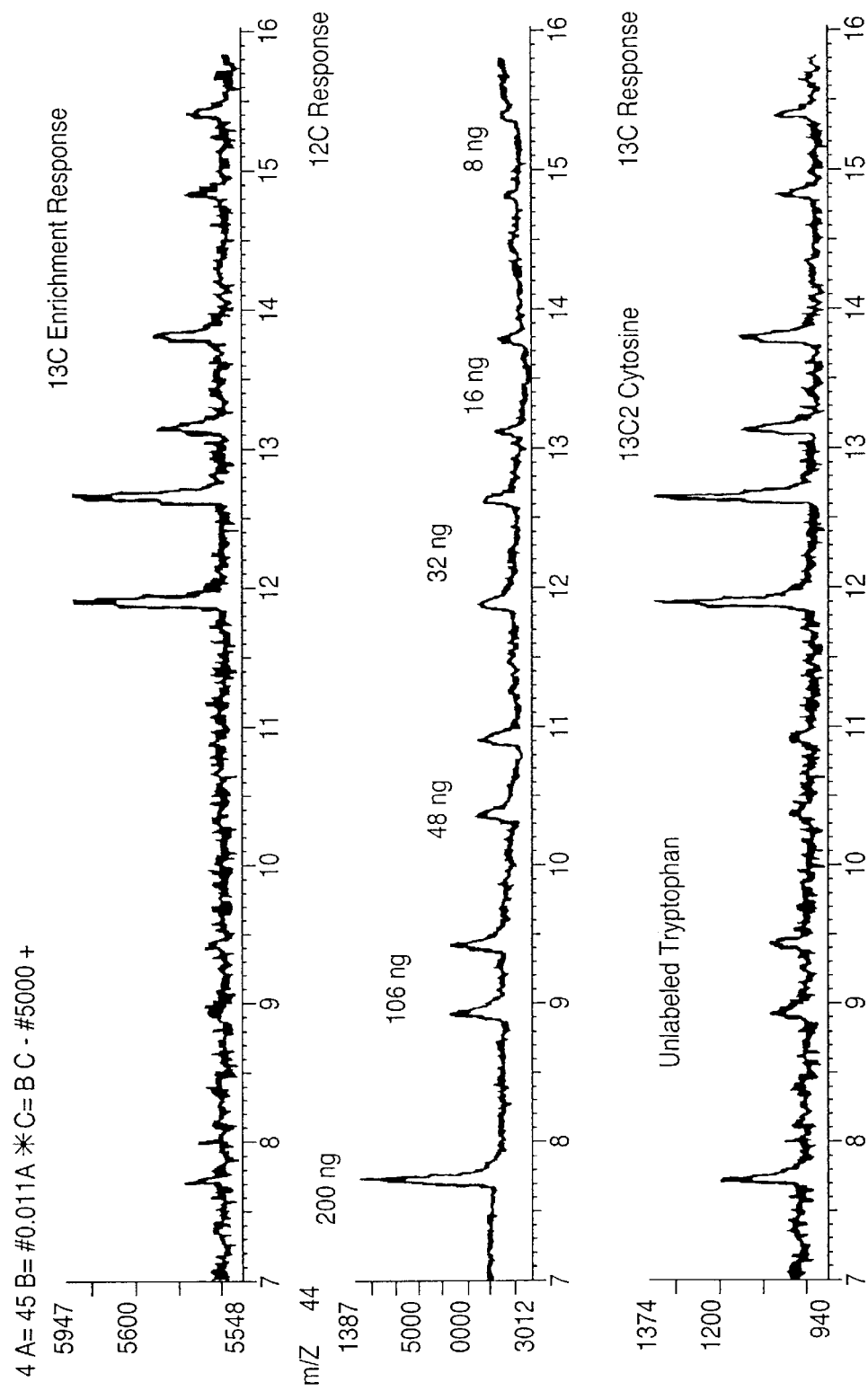
FIG. 3. Flow injection analysis of unlabeled tryptophan followed by $^{13}C$-labeled cytosine with HPLC/CRI-MS.
Figure 5:
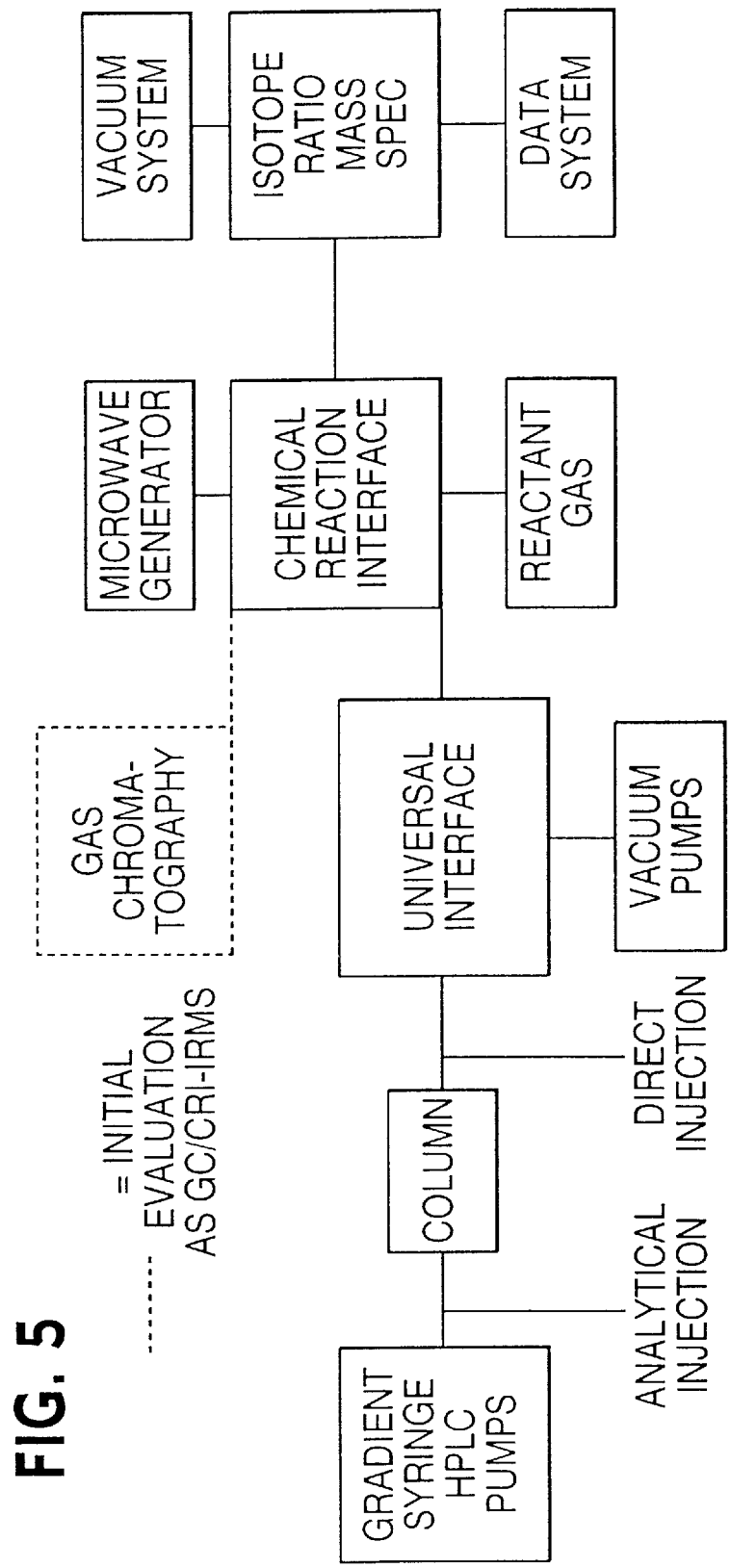
FIG. 5. Block diagram of instrument assembly.

A schematic of the design is shown in FIG. 2. Here, the CRI is interposed between the momentum separator and a Vestec Model 201 quadrupole MS. The inventors have generated isotope-selective data for $^{13}C$ for a variety of molecules. FIG. 3 shows flow injections (i.e.; direct or no column) of unlabeled tryptophan (the left 5 peaks) and labeled cytosine (the right 6 peaks). The unlabeled $^{12}C$ signal is in the m/z 44 chromatogram, and the enrichment trace with essentially all the naturally-occurring $^{13}C$ removed shows only responses for the labeled cytosine for as little as 8 ng.

EXAMPLE 1

The inventors have carried out a metabolism study using $^{15}N$, $^{13}C$-labeled caffeine (A2). Here, 50 mg of labeled caffeine was given orally to a dog and a 24 h urine specimen was obtained. The urine was not purified or extracted in any way, but only filtered through a 0.22μ filter and injected onto the HPLC column. From this, we obtained a general carbon chromatogram at m/z 44 and both enriched $^{13}C$ and $^{15}N$ chromatograms. CRI-MS can simultaneously monitor $^{13}C$ and $^{15}N$ enrichments by just monitoring masses 44–45 and 30–31. This makes using the instrument much easier than if one had to convert the instrument for these two species, and enables certain multiple label experiments where the combined presence of both types of tracers is informative.

Caffeine metabolism includes oxidation to uric acids and demethylation to xanthines. With selected ion traces in the "CRI-MS OFF" mode of operation to determine which enriched CRI-MS peaks belonged to which class of metabolites; e.g., dimethylxanthines, monomethyluric acids, etc., and with authentic standards to differentiate positional isomers by retention times, the metabolic profile shown in FIG. 4 was determined; total carbon is above and enriched $^{15}N$ is below. The results of the HPLC/CRI project are so encouraging that this time was chosen as appropriate to quickly expand the range of applications from those that only require a conventional MS to those where the unique advantages of an isotope-ratio MS will be exploited.

EXAMPLE 2

The inventors use the IRMS to evaluate enzyme-dependent differences in isotopic abundance of analytes from natural origin, and the use of stable isotopes as tracers. Tracer studies are limited by the range of $\delta^{13}C$ values from analytes derived from biologically different sources. For amino acids, the range is about ±4 per mil (S3).

After HPLC/CRI-MS detection, many analytes that require HPLC rather than GC are not amenable to straightforward mass spectrometric identifications. For very polar or unstable molecules, derivatization would be required for electron ionization or chemical ionization. Thermospray might be good for many of these analytes; others might require fast atom bombardment (FAB). FAB might be needed for biological polymers, and yet larger ones could require laser desorption MS.

Isotopic analyses of intact biological macromolecules are valuable in turnover and pool size studies of proteins, DNA, etc. (e.g. A3, P1). Algae that are highly labeled (97% or greater) with $^{13}C$, $^{15}N$, or D are commercially available. From them, protein, DNA, phospholipid, and carbohydrate fractions is obtained by differential precipitation and/or preparative chromatography. The same algal-derived components are obtained with no labeling. Isotopic dilutions of unlabeled macromolecule fractions simulate the situation where one had only fractional labeling of such polymeric species. Samples of varying sizes are injected via a large, say 500 μL, HPLC injection loop with the pump running at 0.5 mL/min and with the output feeding directly into the interface, not using the column. In this way, much more material can be introduced than by capillary GC where the CRI limit of 100 ng/sec is observed. Larger loops providing even longer input times can also be used. With more material, lower enrichment should be determinable. See Analytical Chemistry, Vol. 68 No. 11 (1996) continuous Flow Isotope Ratio Mass Spectrometry Using the Chemical Reaction Interface with Either Gas or Liquid Chromatographic Introduction, Teffera et al., incorporated herein by reference in its entirety.

The following is a model calculation for CRIMS performance when analyzing intact macromolecules. For example, the molecule albumin (MW 69,000 containing 584 amino acids with an average of 0.7 molecules of $N_2$ per amino acid) which is decomposed for isotopic analysis. When unlabeled, the 29/28 mass ratio of $N_2$ as measured with a IRMS would be 0.0073570 (M3). If one nitrogen in its one tryptophan molecule was labeled to the 1% level with $^{15}N$ thus making its $N_2$ isotope ratio 0.013679, the labeled albumin 29/28 ratio would increase to 0.0074103. [To calculate: albumin has 583 AAs having an average of 0.7 molecules of $N_2$/AA with the natural abundance ratio of 0.0073570 plus the one tryptophan with one unlabeled atom of nitrogen and one labeled atom of nitrogen giving one molecule of $N_2$ with isotope ratio 0.013678 (0.003678+0.01), all divided by the total nitrogen-28 produced which is 583×0.7×0.9926421+ 1×0.98632.] The new ratio equals an A.P.E. of 0.0070 $^{15}N$, a value well beyond the previously determined CRI-MS limit of 0.059 A.P.E. for 2 nmol of nitrogen (C2), and easily within the 0.0006 APE minimum found at the 1 $\mu$mol $N_2$ level with an elemental analyzer-IRMS combination (P3). For the measured 31/30 NO ratio, the A.P.E. is 0.0021.

Therefore, the isotopic labeling experiment outlined above is within the range of use of the hardware developed. One should note that it takes only 2.5 nmol of albumin to provide 1 $\mu$mol of N2 or 2 $\mu$mol of NO. In comparison, a GC/standard-MS analysis with suitably derivatized tryptophan gives a prominent fragment ion of mass 375 with an isotope peak at m/z 376 whose abundance is about 30%.

With good precision for a GC/MS result, the level of enrichment which is detectable (i.e.; the 376/375 ratio would increase to 30.63% requiring a precision of <2% for detection).

EXAMPLE 3

In one instance urine specimens from a hamster that was treated with $^2H_4$-acetaminophen are tested. With HPLC/CRI-MS, the acetaminophen urine is examined without deconjugation, to simplify performing metabolism studies. With the CRI, the nature of the conjugate is not important, as the label in a glucuronide, sulfate, amino acid, peptide, or phosphate conjugate is detectable.

EXAMPLE 4

An example of a practical application of the proposed technology involves synthesis of vaccines. A synthetic method for vaccines has been developed that involves linking two macromolecules with adipic acid dihydrazide (C5). The extent of the conjugation reaction cannot be measured in absolute terms because the color-forming reaction currently used yields a product with a different absorptivity with different structures. To meet FDA guidelines for production, an absolute quantitation method is needed. One can easily make the dihydrazide with $^{15}N$, thus a quantitation of $^{15}N$ in the macromolecular product would accurately measure the extent of the reaction. The intact vaccine weight about $2\times10^6$ Daltons, thus it is outside the range of all mass spectrometric methods. Although each of the monomeric units of the polysaccharide contains one nitrogen atom, a model computation shows that the incorporation of $^{15}N$ in this manner is well within the range of measurement of the CRIMS instrumentation.

EXAMPLE 5

The invention improves performance with stable isotopes so that radioisotope use can be diminished. One particular "standard" method that uses radioactivity is in mass balance studies. A labeled substance is given to some biological system and fractions from that system are examined for their label content. Typically this label is $^{14}C$, and scintillation spectrometry effectively counts the amount of label regardless of its chemical form. If one were using an animal, biological specimens like urine, bile, feces, saliva, etc. would be taken. If a cell system, one might count uptake into the cells. The inventor has evaluated the flow introduction HPLC/CRI-IRMS system for this purpose.

In summary, biological instrumentation in the claimed assay improves mass spectrometric detection methods for stable isotopes.

EXAMPLE 6

Metabolite profile studies using stable isotopes.

For the stable isotopes $^{13}C$, $^{15}N$, and $^2H$ (D), a 50 mg dose of suitably labeled phenytoin was administered intravenously to a dog, and a 1% aliquot of the 48 h urine sample was taken for analysis (C1). For each label, metabolites representing well below 1.5% of the total label are identified in the chromatogram. Detection limits from urine of 380 pg/mL of a $^{15}N$-labeled metabolite, 7 ng/mL of a $^{13}C$-labeled metabolite, and 16 ng/mL of a deuterium-labeled metabolite were determined at a signal to noise ratio of 2. This is transformed into on-column amounts of 0.44 pmol of $^{15}N$-labeled phenytoin, 12.3 pmol of $^{13}C$-labeled phenytoin, and 95 pmol of deuterium-labeled phenytoin. Depending on the isotope examined, a linear dynamic range of 250–1000 was observed using CRI-MS.

The analytical characteristic of CRI-MS or continuous flow IRMS is analogous to detection of a radioisotope where a labeled substance is noted regardless of its specific chemical form. Such an experiment directs subsequent studies to qualitatively identify the "flagged" materials that are now known to be metabolites. Once identified, the areas under the peaks in the isotope-selective chromatogram can be used to quantify the metabolite pattern. Because the same decomposition molecule is being identified for each metabolite, this quantitative experiment requires no further calibration; each metabolite does not need to be synthesized to obtain a sensitivity factor if the number of labels in the metabolite is known.

This experiment involves examination of the metabolism of $^{13}C$-labeled tryptophan by hepatoma cells. The labeled material was added to the medium and the cells were incubated for 4 days at which time the supernatant was decanted, extracted and the t-butyldimethylsilyl (TBDMS) derivatives formed. Three $^{13}C$-labeled peaks were found with CRI-MS. Two were also in the starting medium and in scanning experiments were identified as the labeled tryptophan in two different derivatized forms (the bis and tris TBDMS). The one unknown peak was tentatively identified as (indole)-N-formyl-tryptophan on the basis of its mass spectrum. A similar compound and the (amino)-N-formyl isomer were also found in rat urine following intraperitoneal injection of $^{13}C$-labeled tryptophan. This example illustrates how the compound-independent detection capabilities of a CRI-type interface provides the analyst with the opportunity to find totally unexpected results.

The inventors also analyzed a sample which was an extract from an incubation of $^{13}$C-labeled (S)-valproic acid with rat hepatocytes. The samples were trimethylsilylated and chromatographed on a capillary column. By following the enriched $^{13}$CO$_2$ signal we were able to observe a range of oxidation products, but also observed two unexpected metabolites by monitoring the m/z 30 channel ($^{14}$NO). Valproic acid itself does not contain nitrogen, so these may represent previously unrecognized metabolites that have had nitrogen added to the structure, perhaps by conjugation.

This range of experiments shows that GC/CRI-MS is capable of performing well with a wide variety of biologically-derived samples and that it provides an important analytical tool for the scientist studying metabolism.

Experiments evaluating the ability of GC/CRI-MS to perform isotope ratio measurements using phenytoin (C2). For $^{13}$C-labeled phenytoin the detection limits were 10, 3, and 2.5 ng in the presence of 500, 50, and 5 ng of unlabeled phenytoin, respectively. This represents 30–120 pmol of excess 13CO2 from 380–38,000 pmol of total CO$_2$. The lowest molar enrichment quantified was 2.0% which is equivalent to a calculated A.P.E. for this sample of 0.278 or a δ %‰ of 234 (i.e. a 23.4% enrichment of the 1.1% natural abundance). For $^{15}$N-labeled phenytoin the detection limit was 0.3 ng in the presence of each of these three amounts of unlabeled phenytoin. This represents 2.4 pmol of excess $^{15}$NO from 40–4000 pmol of total NO. The lowest molar enrichment quantified was 0.00059 which is equivalent to a calculated A.P.E. for this sample of 0.059 or a δ %‰ of 148. As little as 1 ng of D-labeled phenytoin was quantified in the presence of 500 ng of unlabeled phenytoin. This represents 40 pmol of excess deuterium. The enrichment could not be experimentally determined although its molar enrichment was 0.096%. For all these experiments, coefficients of variation of 3–6% were observed. The principal advantage to be gained with IRMS is the orders of magnitude improved precision, thus allowing correspondingly lower isotope ratios to be measured.

EXAMPLE 8

For detection of $^{13}$C, the production of $^{13}$CO$_2$ in an oxidizing chemical reaction environment is used. Enrichment-only chromatograms can be generated by recognizing that, up to a high (but not infinite) level of approximation, the natural abundance of endogenous materials is fixed and known. The signal observed at M+1 is the sum of naturally abundant isotopes plus any additional contribution by the presence of a molecule with higher-than-natural isotopic abundance. While monitoring both m/z 44 and 45, we can mathematically remove the naturally abundant contribution to the m/z 45 channel by subtracting from it the product of the m/z 44 intensity and the fraction of natural abundance represented by the M+1 of that species (A1). For CO$_2$, the $^{13}$C and $^{17}$O contributions are approximately 0.0119. Therefore, the equation:

$$\text{Enriched } ^{13}\text{CO}_2 = \text{m/z}45 - 0.0119 \cdot \text{m/z}44 \quad (1)$$

nulls out all unenriched peaks in the m/z 45 channel and provides an enrichment-only chromatogram (EOC) selectively showing peaks where the amount of 13C is enriched compared to natural abundance. The channel that monitors $^{13}$C is as complex as the channel that monitors $^{12}$C. In the $^{13}$C enrichment-only chromatogram just the labeled drug, its metabolites, and the internal standard are observed. Although the TIC chromatogram from urine for the control experiment where the dog received no drug was nearly as complex as seen in the $^{12}$C trace, the EOC in is effectively blank.

Generating an EOC uses a special feature of the Teknivent data system, called CALC. CALC allows the algebraic manipulation of one or more channels of data. Simple calculations such as dividing the intensity of one mass by another, as well as more complex actions, can be carried out. The result is a new channel of data that can be plotted, integrated, etc., in whatever ways the original mass channels could be. If Eq. (1) is programmed into CALC, then a $^{13}$C-EOC results. This essential feature has not been implemented on any other manufacturer's data system and explains why our laboratory has exclusively used Teknivent data systems up to this point.

For $^{15}$N, a similar idea is used. The species detected is NO at m/z 30 and 31. With nitrogen, the use of SO$_2$ as a reactant gas shows its most important advantage. The production of NO from the nitrogen contained in an analyte is many-fold higher than when O$_2$ is used as the reactant gas. With SO$_2$, NO is at least as abundant as N2, whereas it is only about 10% of N$_2$ abundance with oxygen. Because of the production of CO, as well as the fragmentation of CO$_2$, m/z 28 and 29 cannot be used to selectively monitor $^{14}$N$^{14}$N and $^{14}$N$^{15}$N. On the other hand, m/z 30 and 31 are due exclusively to nitrogen and allow simultaneous monitoring of $^{13}$C and $^{15}$N in the same run by also acquiring m/z 44 and 45. To generate a $^{15}$N enrichment-only chromatogram, we use the 0.00403 natural abundance of m/z 31 for NO as the multiplier for the m/z 30 intensity prior to subtracting from the observed m/z 31 signal.

TABLE 1

Summary of CRIMS chemistries.

| Element or isotope | Product* | Mass[a,b] | Reactant | Reference |
|---|---|---|---|---|
| $^{1,2}$H | $^{1,2}$HF | 20, 21 | NF$_3$ | 24, 25 |
| H | H$_2$O | 18 | SO$_2$[c] | 9 |
| $^2$H | $^2$H$^1$H | 3.022 | H$_2$ | 9 |
| $^{12,13}$C | $^{12,13}$CO$_2$ | 44, 45 | SO$_2$ | 9 |
| C | CO | 28 | | 9 |
| $^{14}$C | $^{14}$CH$_4$ | 18.034 | H$_2$ | 4, 5 |
| C | CH$_4$ | 16 | | 5, 9 |
| | C$_2$H$_2$ | 26 | | 5, 9 |
| | HCN | 27 | N$_2$ | 5 |
| $^{12,13}$C | $^{12,13}$CF$_4$ | 69, 70(CF*$_3$)[d] | NF$_3$ | 24, 25 |
| $^{14,15}$N | $^{14,15}$NO | 30, 31 | SO$_2$ | 9 |
| | N$_2$ | 28, 29 | | 6, 9 |
| | NO$_2$ | 46, 47 | | 6, 9 |
| N | HCN | 27, 28 | H$_2$ | 5, 9, 19 |
| O | H$_2$O | 18 | H$_2$ | 19 |
| $^{16,18}$O | C$^{16,18}$O | 28, 30 | | 19[e] |
| P | PF$_5$ | 107(PF$_4$*) | NF$_3$ | 24, 25 |
| S | S$^{35,37}$Cl | 67, 69 | HCl | 20 |
| | SF$_6$ | 127 (SF$_5$*) | NF$_3$ | 24, 25 |
| Cl | H$^{35,37}$Cl | 36, 38 | SO$_2$ | 21, 22 |
| | F$^{35,37}$Cl | 54, 56 | NF$_3$ | 24, 25 |
| Se | $^{80}$Se$^{35,37}$Cl | 115, 117 | HCl | 23 |
| Br | H$^{79,81}$Br | 80, 82 | SO$_2$ | 21 |

[a]Only those species that are useful for more than one isotopic variant are indicated with multiple masses.
[b]Where the exact mass is indicated, high resolution is required to obtain the selective result.
[c]Where SO$_2$ is indicated as the reactant gas, other oxidizing gases such as O$_2$ will give the same products, but with different yields.
[d]We presume that $^{13}$C-selective detection is possible, but have not yet demonstrated it.
[e]O$^{18}$ detection is from this laboratory (unpublished).

EXAMPLE 9

The inventors have also analyzed selected elements or isotopes using a direct probe as a means of introducing samples into CRI-MS. The inventor's published work on this area examined the sulfur content of proteins (A3). A linear signal was observed for the $SO_2$ produced from the oxidation of polymethionine for amounts down to 20 ng. A good correlation (r=0.80) between the theoretical and observed S/C atomic content at the 1 μg level of 12 proteins of varying composition was found.

EXAMPLE 10

In cancer chemotherapy, this test provides information regarding stem-cell reserve and could prevent severe neutropenia secondary to chemotherapy. Included is a model for transplantation, and monitoring lymphocyte function in transplantation medicine. Another immunological application examines patients with drug hypersensitivities. Finally, the invention has applications in the study of aging.

It is estimated that 80% of elderly men are hyposomatomenemic and the increasingly frequent use of growth hormone in both aged and younger populations points to new research areas. Growth hormone reverses the thymic involution of aging and increases hematopoiesis from bone marrow cells.

The inventors have devised a nonradioactive, nontoxic method to measure DNA synthesis rates. This fundamental measurement of cellular replication, so readily performed in experimental systems with $^3$H-thymidine ($^3$H-dT) or bromodeoxyuridine (BrdU), is not readily measured in the clinical setting. The doses of radioisotope and the subsequent incorporation into the cell nucleus inhibit its use. Although increasingly popular, halogenated pyrimidines, such as BrdU, are toxic and mutagenic. In contrast, stable isotopes as tracers have a 50+ year history of safety. Using stable-isotope labeled substances, i.e., glycine as a precursor of de novo purine biosynthesis, averts any concerns about safety and would encourage the clinical use of a fully-developed method to study fundamental processes, diseases, and therapies that affect cellular proliferation.

For these measurements, Chemical Reaction Interface/Mass Spectrometry (CRIMS) was used which has evolved from a basic concept into a selective, sensitive, and versatile technique by which targeted isotopes or elements can be monitored in studies of metabolism (A1). CRIMS parallels the use of radioisotopes in that this monitoring takes place without concern for the chemical structures in which the targeted species exist. Using CRIMS, intact analytes are first decomposed to their elemental species in a high-temperature electronic plasma and then interact with atoms of a reactant gas to form a set of new, small, polyatomic species that are detected by a mass spectrometer. The presence of a given polyatomic species signifies the presence of a particular element, the abundance of that species quantifies it, and the isotopic signature of that species can differentiate enriched from endogenous materials.

Previously, the inventors have compared how well HPLC/CRIMS can detect stable isotopes in a drum metabolism study with the standard form of measurement that uses $^{14}$C and radioactivity monitoring (A2). Following administration of a mixed dose of both radioisotope and stable-isotope labeled tirilazad, a parallel set of high-performance liquid chromatographic analyses for drug metabolites in bile samples from monkey and dog was carried out. The comprehensiveness of detection, chromatographic resolution, sensitivity, signal/noise, and quantitative abilities of CRIMS were compared with radioactivity monitoring (RAM) and in no case was RAM superior. With HPLC/CRIMS, stable isotopes such as $^{13}$C and $^{15}$N can be comprehensively detected and quantitative patterns of drum metabolism from biological fluids can be produced that mirror the results when $^{14}$C is used. Therefore, stable isotopes may be substituted for radioisotopes in studies of metabolism where the ability of the latter approach to detect a label independent of the structures in which the label appears has been the primary reason for continuing to use a hazardous and expensive tracer.

Beyond the capabilities of conventional mass spectrometers is a special configuration of a mass spectrometer optimized for making stable-isotope abundance measurements, the multicollector isotope ratio mass spectrometer (IRMS). An IRMS is designed to accept gaseous samples, such as $CO_2$, ionize this gas with high efficiency and transmit the appropriate ions to a multiple collector that monitors two or three ions at the same time. The use of IRMS allows measurements of natural variations in the abundance of $^{13}$C and $^{15}$N (B5), and extends the range of tracer incorporation orders of magnitude below what is accomplished with a conventional GC/MS or HPLC/MS system (G2 and B3). Before CRIMS, coupling chromatography to an IRMS involved a combustion interface (B5). The inventors have joined chromatography with IRMS using their chemical reaction interface (T1). The most important aspect of this development was to construct a continuous-flow HPLC/IRMS combination. With the present system, the precision of isotope ratio measurements with HPLC introduction is equal to the same system with GC introduction (T1).

Tritiated thymidine is the standard method for measuring DNA synthesis rates. Specific effects of agents that stimulate cell proliferation, or slow the progression through the cell cycle can be quantified. The halogenated pyrimidine techniques developed for flow cytometry and microscopy have almost replaced autoradiographic techniques with $^3$H-dT in cell kinetic studies. The most widely used is the BrdU technique that is sensitive, fast, and easy to carry out. The essence of the procedure is to pulse label cells with BrdU by a short incubation in vitro or by a single injection in vivo. Then the cells are stained using a monoclonal antibody against BrdU and analyzed using a flow cytometer or microscope. In cell cultures, continuous exposure to BrdU may entail a plethora of adverse effects on cellular functions, including metabolic changes due to alterations in the balance of nucleotide pools, direct DNA damage, and alterations in DNA-protein interaction (o1).

The de novo biosynthesis of nucleotides is well described (L2). Both carbons and the nitrogen of glycine are incorporated into purines (See FIG. 6). A possible problem here is that $C_2$ of glycine is directly converted into a tetrahydrofolate derivative and intermixes with $C_2$ and $C_3$ of serine. One of those serine carbons might also subsequently become the one carbon group in folate. Folate is involved in de novo thymidine biosynthesis. As will be described, it is important that dT is not labeled by the tracer glycine molecule, because the $^{13}$C isotope ratio of dT will serve as a control for any enrichment found in deoxyguanosine or deoxyadenosine. Therefore, the first studies use 1-$^{13}$C-glycine as the purine precursor.

Studies were begun with HEP G2 human hepatoma cells. HEP G2 cells are frequently used for metabolic studies, in particular studies of lipids and lipoprotein synthesis (J1). These cells grow well and to good densities, thus making them practical to use.

EXAMPLE 11

The probe 1-$^{13}$C-glycine is incorporated into purines via de novo biosynthesis. The human hepatoma cell line HEP G2 was grown in medium containing 1-$^{13}$C-glycine, the cells were harvested at various times and the DNA extracted. Following hydrolysis to the nucleosides, a reversed-phase HPLC separation was used to provide separate peaks for deoxythymidine (dT), deoxyadenosine (dA), and deoxyguanosine (dG). The HPLC effluent was continuously fed into a chemical reaction interface and an isotope ratio mass spectrometer (HPLC/CRI/IRMS). The isotope ratio of the $CO_2$ produced in the CRI was used to monitor for enrichment. The cells were grown continuously for five days in labeled medium, and also in a one-day pulse labeling experiment where the washout of label was observed for the subsequent nine days. As predicted from the role of glycine in de novo purine biosynthesis, the isotope ratio of the pyrimidine dT did not change. However, for the two purines, dA and dG, the characteristic log-growth behavior of the cells were observed in their $^{13}C/^{12}C$ ratios and good agreement in the doubling time was obtained for each type of experiment. Parallel experiments that measured the HEP G2 doubling time in culture using direct cell counts and tritiated thymidine incorporation were carried out to verify the method. The use of 1-$^{13}$C-glycine and the HPLC/CRI/IRMS approach forms the basis of a method that can measure DNA synthesis rates in humans using a nonradioactive, nontoxic tracer.

Cell Culture

HEP G2 cells were grown in 25 mL of supplemented phenol red-free Dulbecco's minimal essential media (Sigma Chemical Co., St. Louis, Mo.) by plating 2.5 to 10×10$^6$ cells into 150 cm$^2$ culture flasks. Each liter of the media was supplemented with 10% fetal calf serum, 1% penstrep, 4.5 g of glucose, 2.7 g of sodium bicarbonate, 0.58 g of glutamine, and 0.11 g of pyruvate. The final pH was adjusted to 7.1–7.3. Fetal calf serum and penstrep were obtained from Biofluids (Rockville, Md.). All other chemicals were cell culture grade from Sigma. This medium contains 0.4 mM glycine. With $^{13}$C labeling, various amounts of 1-$^{13}$C-glycine (99% Cambridge Isotope Laboratories, Andover, Mass.) were added to achieve the desired level of enrichment. The cells were cultured at 37° C., with 95% relative humidity and a $CO_2$ level of 5%. The cells were fed every two days with 25 mL of media and were split one-to-ten every week.

DNA Isolation

DNA was extracted by using the Puregene DNA isolation kit (Gentra Systems, Inc., Minneapolis, Minn.). All enzymes used were obtained from Boehringer Mannheim (Indianapolis, Ind.). Two or three flasks containing a total of 1–2×10$^8$ cells are harvested on desired days and washed with PBS solution. The cells are transferred to a 50 mL tube and centrifuged at 500×g for 5 minutes. The supernatant is removed and 30 mL of cell lysis buffer are added. Next, proteinase K is added to a final concentration of 100 μg/mL and incubated 2 hours at 37° C. Then, RNase at a final concentration of 20 μg/mL is added and incubated for two hours at 37° C. Then, 10 mL of the Puregene's protein precipitation solution is added to the lysed cells, vortex for 30 s, and centrifuge at 2,000×g for 10 minutes. The supernatant containing the DNA is poured into a new tube containing 25 mL of iPrOH (leaving behind the protein pellet), and then the sample is mixed by inverting gently 50 times until the white thread of DNA is visible and again centrifuge at 2,000×g for 10 minutes. DNA will form a white pellet. The supernatant was poured off and the tube drained on filter paper. Then, 30 mL of 70% EtOH, is added, the tube is inverted several times to wash the DNA, centrifuge at 2,000 ×g for 5 minutes, and carefully pour off the EtOH. Then, the tube is drained on filter paper, and the sample is allowed to air-dry for 5 minutes. Finally, 2.5 mL of $H_2O$ is added and the DNA is rehydrated overnight (or heat at 65° C. for one hour).

Digestion of DNA

DNA samples were enzymatically hydrolyzed to nucleosides using a modified procedures by described by Saris, et al (S2). All enzymes used were also from Boehringer Mannheim. The DNA is denatured by heating in boiling water for 3 minutes, then chilled rapidly with ice water. To a solution of denatured DNA (0.5 mg/mL), the following were added (per mL): 100 μL of 10×buffer (20 mM $MgCl_2$, 10 mM $ZnCl_2$, 500 mM Tris, pH 7.2); 10 μL DNase I (0.5 U/μL); 10 μL Nuclease P1 (0.5 U/μL); and 20 μL (4 mU/μL) of phosphodiesterase. The solution was incubated for two hours at 37° C. Then 1 μL of 10 M ammonium acetate (pH 9.0) and 5 μL of alkaline phosphatase (1 U/μL) were added and incubated for another two hours at 37° C.

Nucleoside Purification and Analysis

Figure 7:
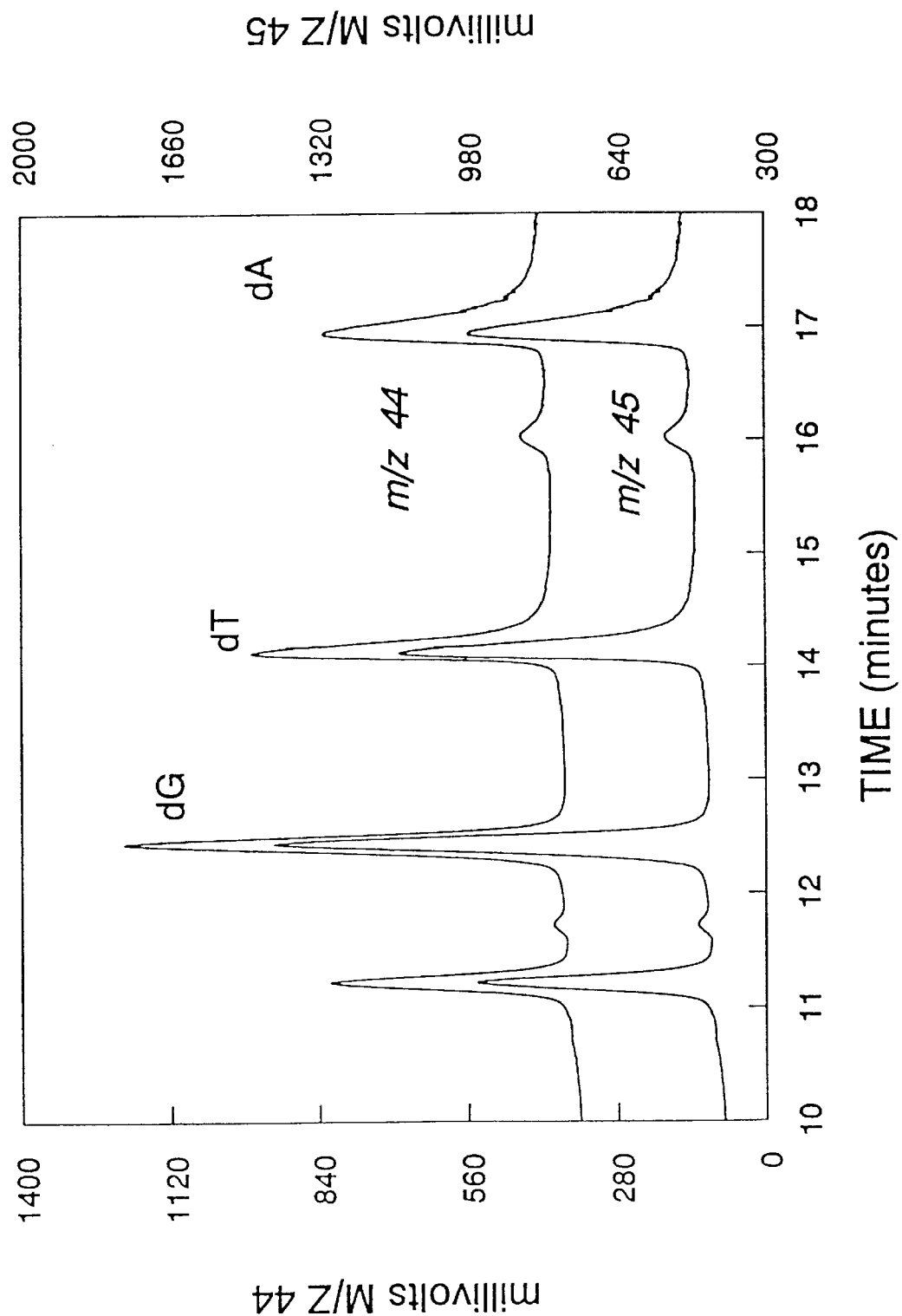
FIG. 7 shows an HPLC/CRI/IRMS chromatogram of DNA nucleosides extracted from HEP G2 cells. The peak eluting at 11.2 minutes is unknown. The amplifier for m/z 45 has a 100×gain compared with m/z 44.

HPLC solvents were obtained from EM Science (Gibbstown, N.J.) with less than 0.1 ppm evaporation residue. All HPLC experiments were conducted with a pair of Isco Model 260D syringe pumps (Isco Inc., Lincoln, Nebr.) coupled with a Gilson Model 811C Dynamic Mixer (Gilson Co. Inc., Middleton, Wis.). Samples were dissolved in deionized water and injected using a Model 7125 valve (Rheodyne, Coati, Calif.) with a 100 μL loop. The nucleoside mixture was filtered with 0.22 μm nylon filter (Micron Separations Inc., Westboro, Mass.) and purified using a Waters (Milford, Mass.) Nova-Pak $C_{18}$ column (8×100 mm, 60 Å). The mobile phase A was 5 mM ammonium acetate (pH 4.0) and mobile phase B was 50:50 acetonitrile/water (v/v). The solvent conditions were 0% B for 5 minutes then a linear gradient to 90% B in 5 minutes. The flow rate was 2 mL/min. The nucleoside portion was collected and concentrated using a Speed Vac. The nucleosides were injected into a 100 μL loop and separated using a Supelco (Bellefonte, Pa.) 18-S column (4.6×250 mm, 5 μm) before entering the CRI/IRMS. The gradient used was from 5% to 20% B in 15 minutes (linear) at 1 mL/min. As seen in the accompanying chromatogram (FIG. 7), excellent separations were obtained with this procedure. Part of the purification removes a major impurity, but that also mostly removes dC. dT is unaffected by the purification so that dT becomes the preferred internal standard for isotope ratios when the glycine is the labeled test substance.

The isotopic analysis was carried out using a Finnigan/MAT Delta S IRMS (Finnigan/MAT, San Jose, Calif.) to which HPLC/CRI interface (T1) was added. The CRI reactant gas was UHP oxygen (Matheson Gas Products, East Rutherford, N.J.). The integration of each peak used a slope sensitivity of 1 mV/s, a value that was found to give the most reproducible values. Most samples were analyzed 3–5 times and the standard deviations plotted.

Measurement and Kinetic Analysis of Growth and Decay

Experiments were carried out where 33% enrichment with 1-$^{13}$C-glycine was used. The isotope ratio of an internal standard, 5'-fluoro-2'-deoxyuridine (Sigma), was determined independently ($\delta^{13}C = -25.3‰$) and initially $\delta^{13}C$ values for the nucleosides were based on that isotope ratio. High precision IRMS data are conventionally expressed per mil (‰), rather than percent. The data are expressed as $\delta^{13}C‰$ computed as $1000 (IR-IR_{PDB})/IR_{PDB}$ where PDB is an international standard isotope ratio (IR$_{PDB}$)= 0.0112372. From the results of this preliminary experiment, there was defined a lower degree of enrichment. The second study followed growth of label over five days during continuous incubation with glycine enriched to 3.3%. The third study used a one-day pulse of 9% enriched glycine and examined the washout of the incorporated label over the next nine days.

Data from these experiments were fit with the suitable exponential growth or decay equation. The curve-fitting procedure in SlideWrite Plus for Windows, Version 4.0 (Advanced Graphics Software, Inc., Carlsbad, Calif.) was used to obtain the parameters of these equations.

One of the two methods used to generate "conventional" data regarding the growth rate of HEP G2 cells was to do a series of cell counts during a normal incubation of these cells. After trypsinization, the cells were pelleted and resuspended to give approximately a 200,000 cell/mL concentration. A 100 μL aliquot of that suspension was diluted in 9.9 mL of Isoton II (Coulter Corp., Miami Fla.). The cells were counted using a Coulter counter ZM.

The second method to generate comparable data regarding the rates of cell growth was to use tritiated thymidine. The medium of HEP G2 cells was supplemented with 0.1 μCi/mL of $^3$H-dT (Amersham Life Science, Arlington Heights, Ill.) and 1 μM unlabeled thymidine. After one day, some cells were transferred into medium that did not contain $^3$H-dT. At various time points during the incubation, the medium was removed and the adherent cells washed three times with PBS and the cells scraped into 1 mL of ice cold PBS. The cell suspension was treated with 1.2N PCA and the precipitate was collected, washed three times with 0.2 N PCA, and solubilized in 1N NaOH (0.5 mL). An aliquot was counted in acidified scintillation medium. These data were also analyzed with exponential growth or decay equations as was done for the labeled glycine experiments.

Figure 8:
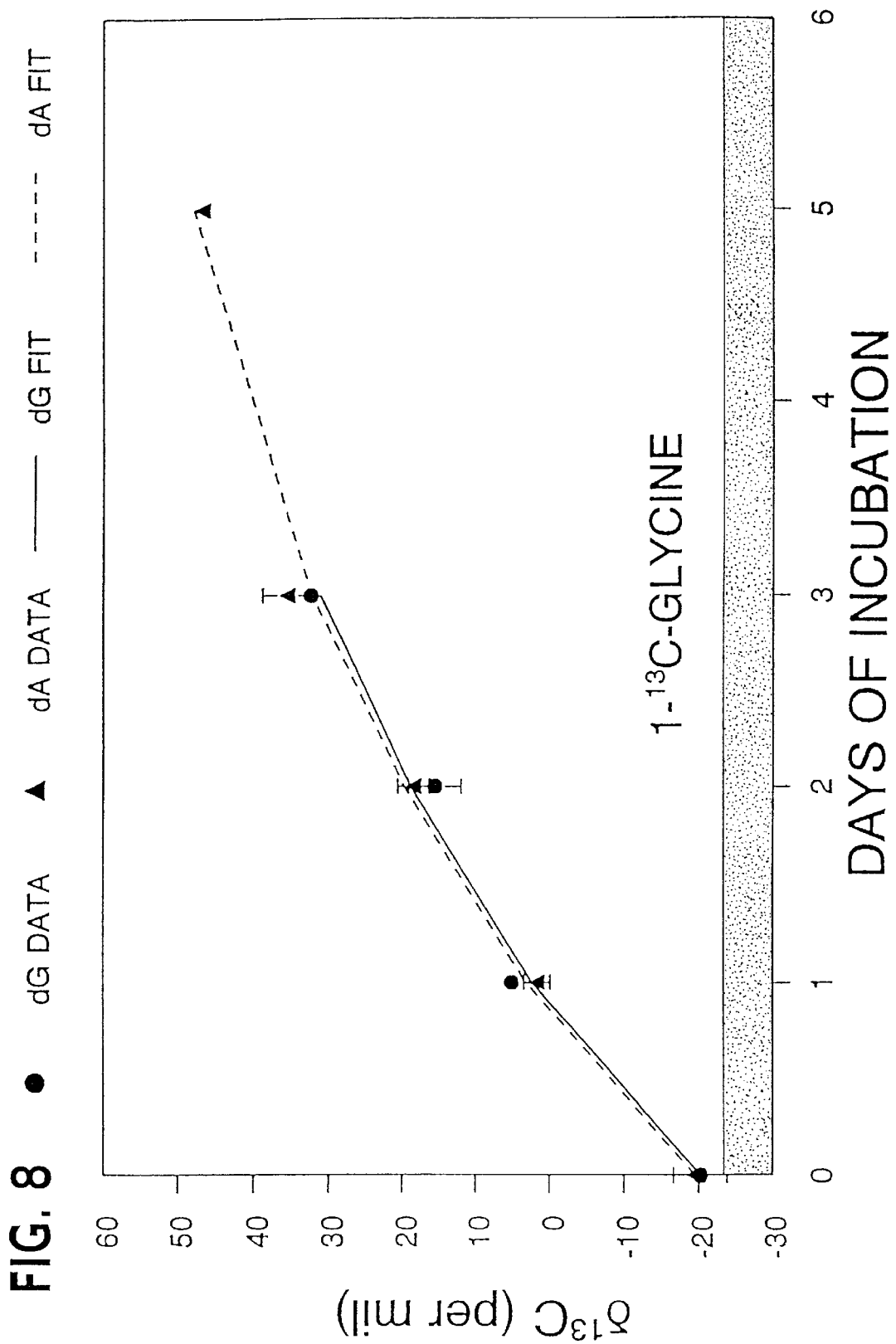
FIG. 8 shows the growth of $^{13}C$ in dA and dG in the DNA from HEP G2 cells during continuous isotopic labeling with 1-$^{13}C$-glycine. No data for dG on Day 5 was obtained. The fit is to the equation: $\delta^{13}c(t)=\delta^{13}C(ss)\times(1-e^{-kt})$. The correlation coefficient was 0.994 for dA and 0.986 for dG.

In the studies with 33% labeled glycine, dA enrichment rose to a δ$^{13}$C of +375%‰ and dG rose to +321%‰ after four days of incubation. From the growth experiment with 3.3% 1-$^{13}$C-glycine (FIG. 8), the doubling time for the HEP G2 cells to be 2.3±0.4 days using the kinetics of dA enrichment and 2.2±1.2 days using dG kinetics was measured. The lesser accuracy of the dG component of the growth experiment is due to the inability to obtain a measurement for dG on Day 5, thus the fit involves one less data point.

The errors reported are the SEs for the fitted parameters. The projected steady-state enrichments were +66%‰ and +63%‰ respectively. In addition, the isotope ratio of dT was measured. Over these five days, its δ$^{13}$C value was constant at −15.8%‰±1.2 (mean±SD, N=7) compared to the value on Day −1 of −15.9±2.2 (N=6). This observation showed that 1-$^{13}$C-glycine is selectively incorporated into purines and not into pyrimidines. Consequently, it is suggested to use the measured control isotope ratio for dT to calculate dG and dA enrichment at any time in a given experiment.

Figure 9:
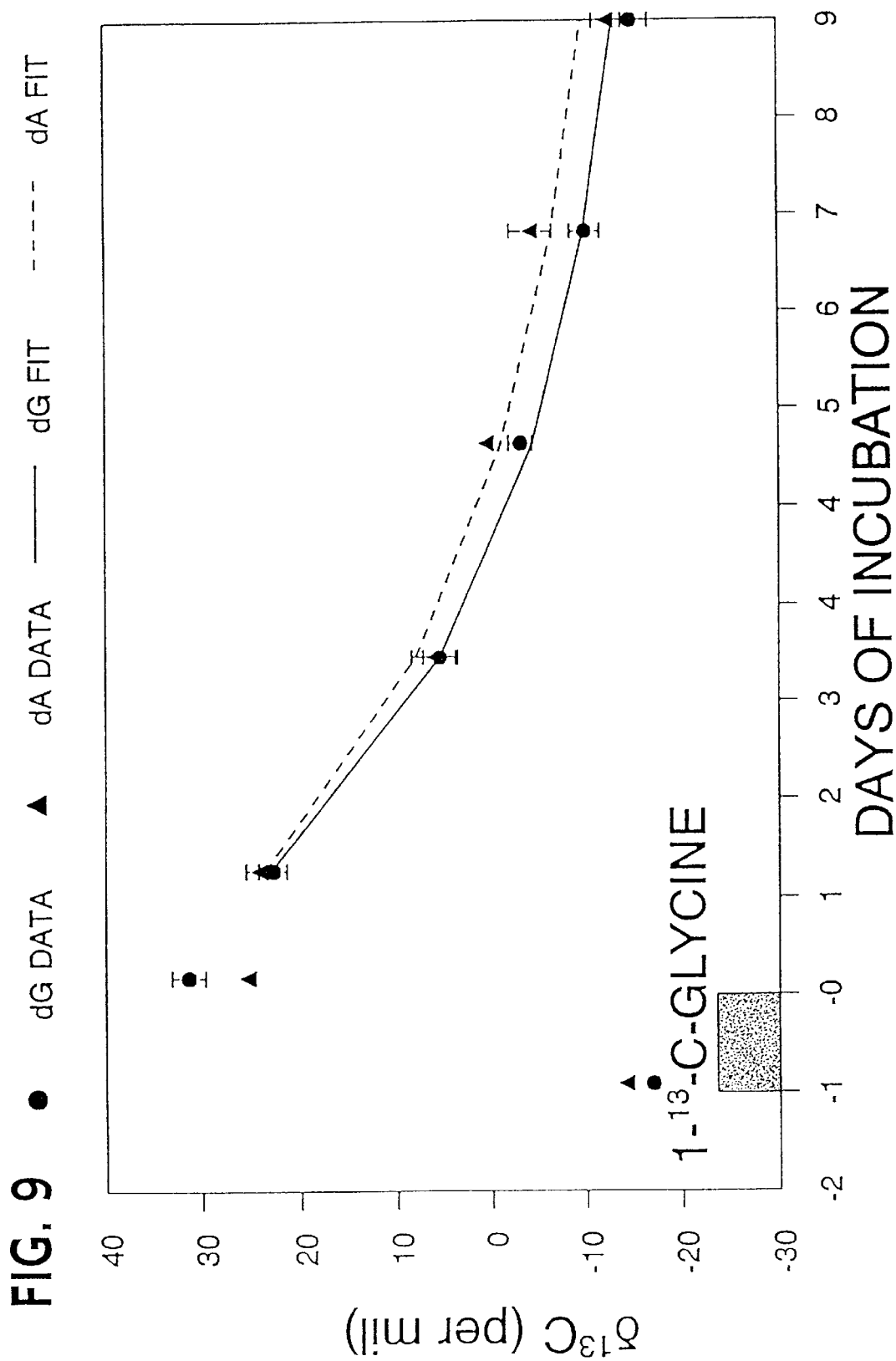
FIG. 9 shows the wash out of $^{13}C$ in dA and dG in the DNA from HEP G2 cells following a one-day pulse of labeled glycine. The data were fit using the equation: $\delta^{13}C(t)=\delta^{13}C(0)\times e^{-kt}$. The points for Day 0 were not used for the fit. The correlation coefficient was 0.974 for dA and 0.994 for dG.

From the wash out experiment (FIG. 9), doubling times were determined to be 2.6±0.3 days for dA and 2.4±0.1 days for dG. Day 0 data was not used because the fit was considerably better without it. The assumption that all the unincorporated label was fully and instantly washed out seems not to be valid.

Figure 10:
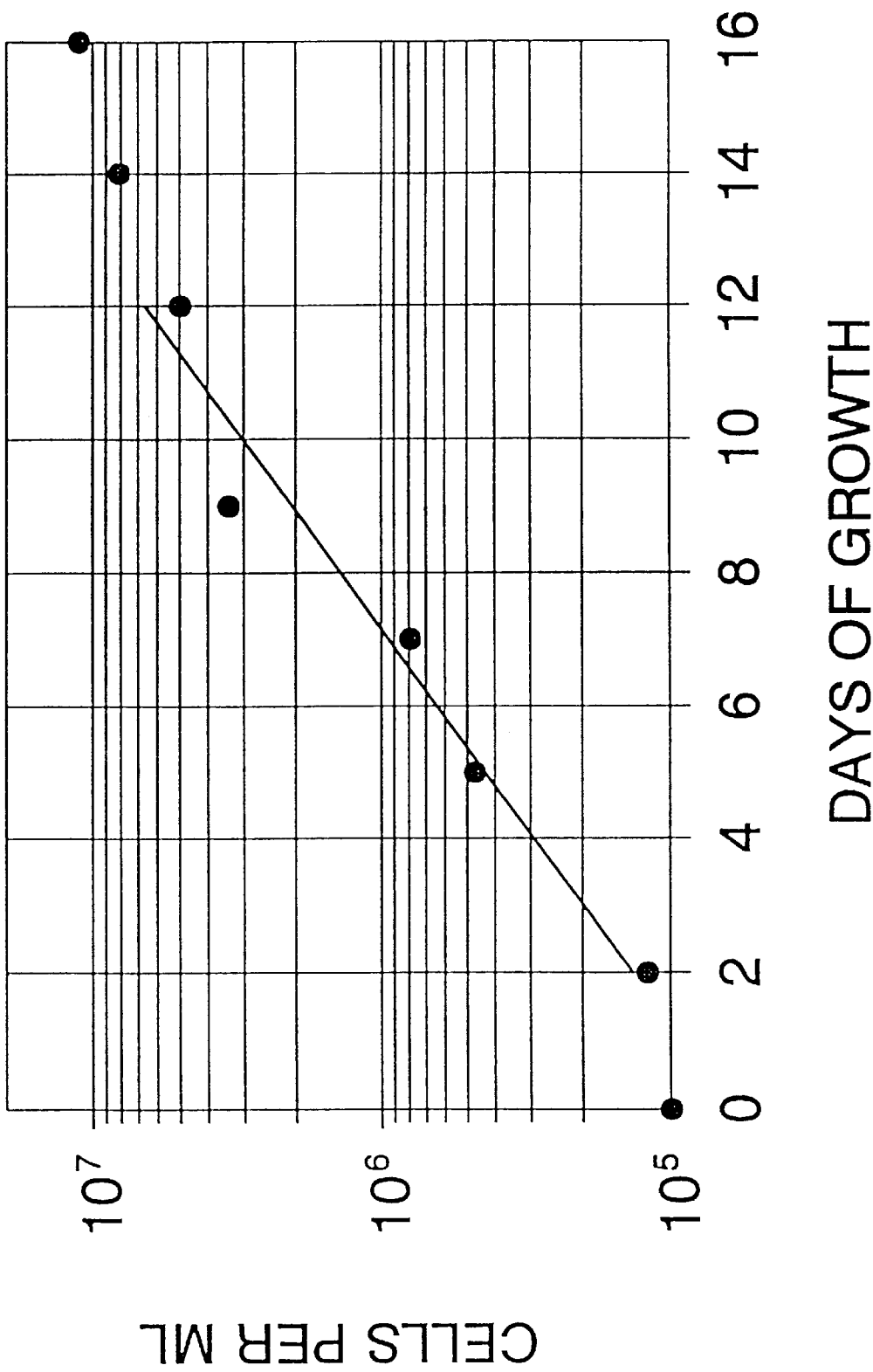
FIG. 10 shows the growth curve of HEP G2 cells in culture. The fit to log growth between days two and 12 is also shown. The correlation coefficient was 0.958.
Figure 11A:
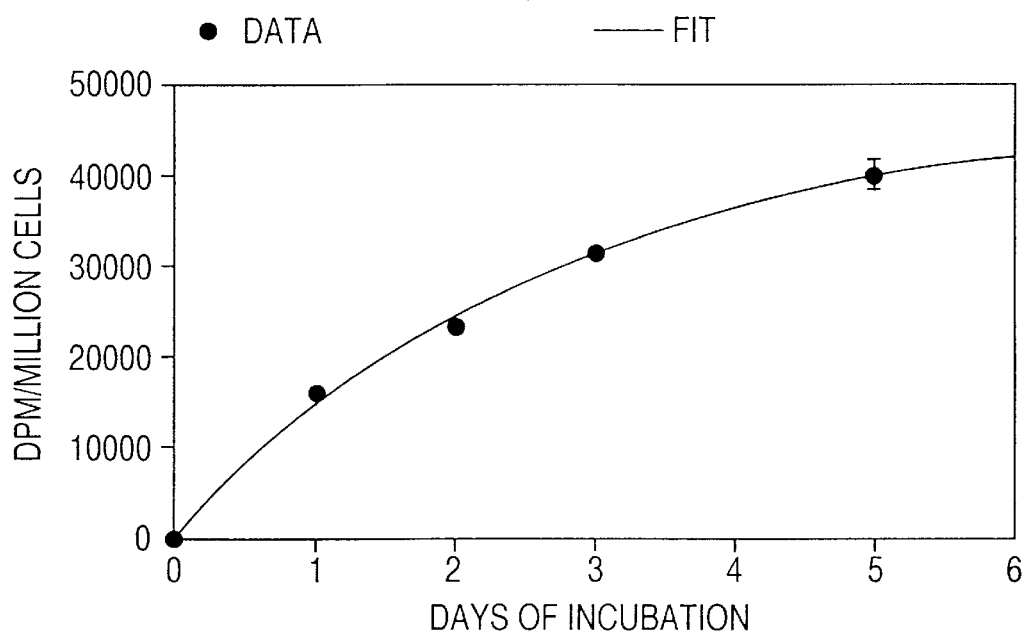
FIG. 11 shows Growth (Panel A) and wash out (Panel B) of $^3H$-thymidine incorporation into DNA in HEP G2 cells grown in culture. The lines are fits to exponential growth and decay (see FIGS. 8 and 9). The regression coefficient was 0.997 for growth and 0.998 for decay.
Figure 11B:
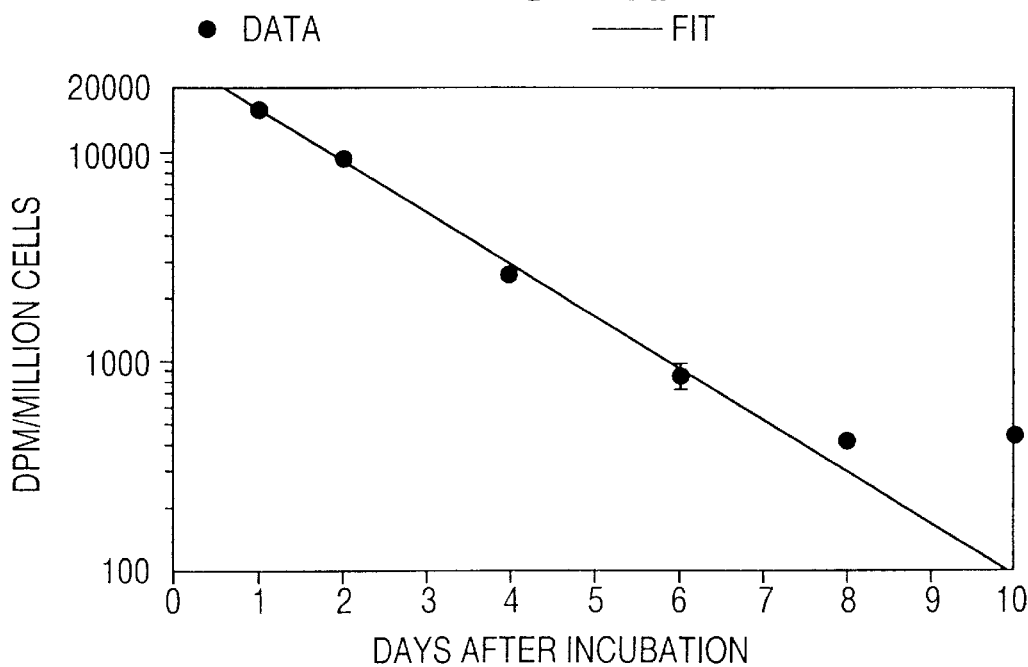

From the log-linear portion of the cell growth curve (FIG. 10), the doubling time was estimated as 1.7±0.2 (SE) days, a value comparable to that calculated from 1-$^{13}$C-glycine incorporation studies. The experiments using $^3$H-dT also were well described by these equations (FIG. 11). The half-lives for growth and decay were 1.9±0.2 and 1.23±0.04 days, respectively.

The validity of the glycine method for measuring DNA synthesis rates is established by several components of the experiments. Most important, whether observing incorporation of label, or the wash out of label, the quality of fits to the first-order equations used were excellent. The correlation coefficients ranged from 0.974 to 0.994. Furthermore, the results from the growth and wash out components were consistent with each other using either nucleoside. The experiment where the cells were counted gave a value for doubling time that was somewhat faster than predicted by glycine. Finally, in the growth phase, the $^{13}$H-dT experiment generated at t½ that also was consistent with the 1-$^{13}$C-glycine data and the cell-count study. The value for decay is rapid compared with the cell counting and 1-$^{13}$C-glycine data.

Seven measurements are combined in FIG. 12. 1-$^{13}$C-labeled glycine is an effective means to measure the synthesis rate of DNA in growing cell populations.

Figure 6:
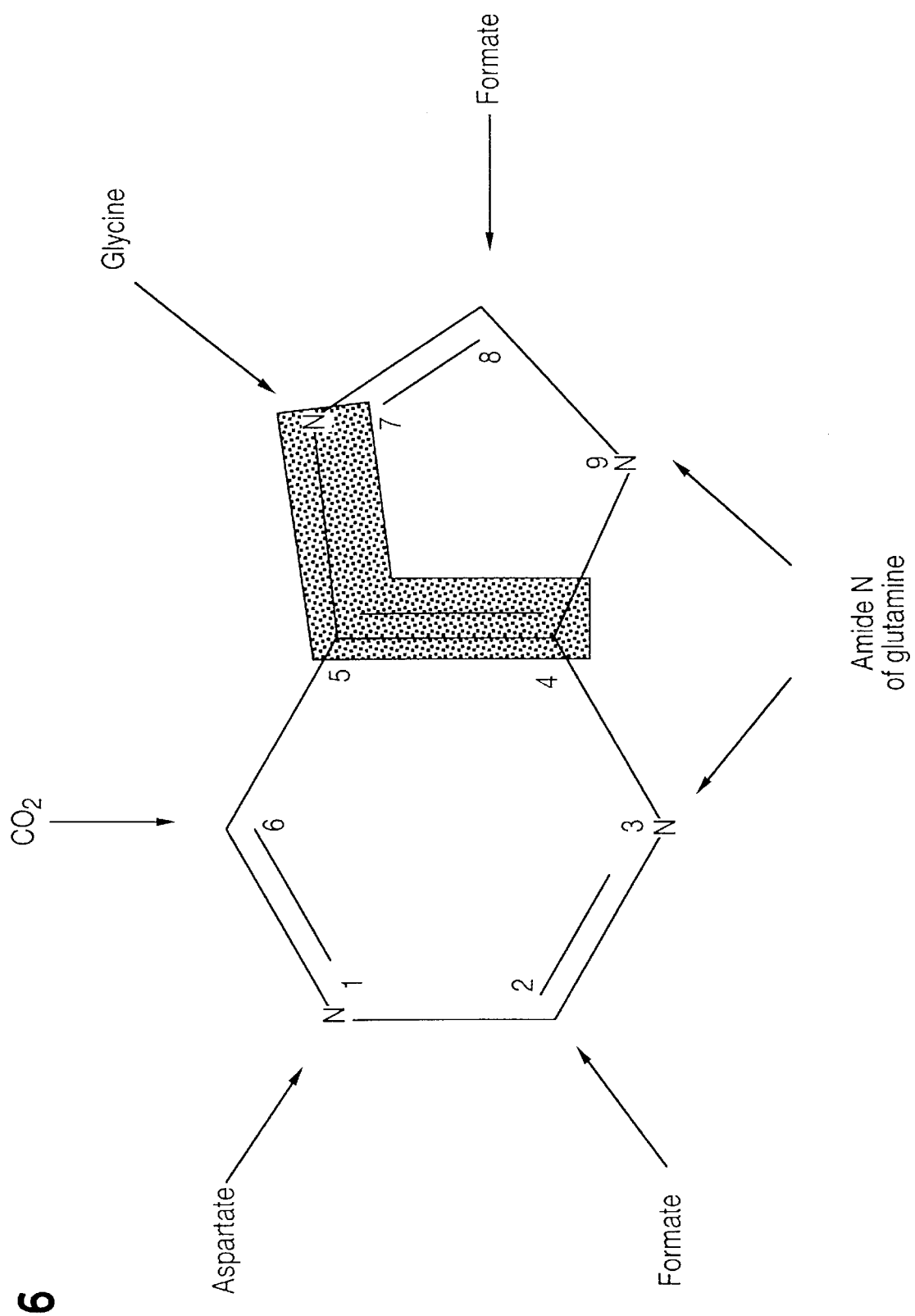
FIG. 6 shows origin of carbon and nitrogen atoms in purines (after Lehninger) (L2).

It is known that δ$^{13}$C values after depending on diet (K1). Such variations make observing small changes difficult because a baseline needs to be established for each subject. Finding that 1-$^{13}$C-glycine does not affect dT means that dT may be an internal standard for purine measurements in humans. As FIG. 6 shows, the carbons in purines come from a variety of sources. The de novo biosynthesis of pyrimidines involves different carbon sources; aspartate and $CO_2$ with the thymidine methyl group coming from $N^5,N^{10}$-methylene-tetrahydrofolate (L2). Ultimately, the use of dT as an internal isotopic standard will need to be further validated by examining the dT vs. dA and dG isotope ratios in populations of control subjects.

In addition the method of the invention can advantageously be used for measuring DNA synthesis rates in surgically-obtained tissues grown in vitro with radioactive labels such as benign vs. malignant tumors; growth fractions in intenstinal cells and in assessing tumor virulence.

REFERENCES

A1. Abramson, F. P. *Mass Spectrom. Revs.* 1994, 13: 341–356.

A2. Abramson, F. P.; Teffera, Y.; Kusmierz, J.; Steenwyk, R. C.; Pearson, P.G. *Drug Metab. Dispos.* 1996, 24, 697–701.

A3. Abramson, F. P. and Markey, S. P., Mass spectrometric analysis of sulfur in microgram quantities of biological macromolecules using a reaction interface; Biomed. Environ. Mass Spectrom. 13: 411–415 (1986).

A4. Abramson, F. P., McLean, M, and Vestal, M., Selective stable-isotope detection with mass spectrometry following gas or liquid chromatographic separation. In press, Proceedings of the International Isotope Society Meeting, Toronto Canada, 1991.

A5. Arends, J. and Bier, D. M., Labeled amino acid infusions of in vivo protein synthesis with stable isotope tracers and gas chromatography-mass spectrometry. Analyt. Chim. Acta 247: 255–263 (1991).

B1. Barrie, A., Bricout, J., and Koziet, J. Gas chromatography-stable isotope ratio analysis at natural abundance levels. Biomed. Environ. Mass Spectrom. 11: 583–588 (1984).

B2. Berthold, H. K.; Crain, P. F.; Gouni, I.; Reeds, P. J.; Klein, P. D. *Proc. Nat. Acad. Sci.* 1995, 92, 10123–10127.

B3. Bier, D. M.; Matthews, D. E. *Federation. Proc.* 1982, 41:2679–2685.

B4. Boni, R. L., Heyes, M. P., Bacher, J. D., Yergey, J. A., Ji, X.-J., Abramson, F. P., and Markey, S. P., Stable isotope-labeled tryptophan as a precursor for studying the disposition of quinolinic acid in rabbits. Adv. Exp. Biol. Med. 294: 481–484 (1991).

B5. Brand, W. A. *J. Mass Spectrom.* 1996, 31: 225–235.

C1. Chace, D. H. and Abramson, F. P., Selective detection of carbon-13, nitrogen-15, and deuterium labeled metabolites by capillary gas chromatography-chemical reaction interface/mass spectrometry. Anal. Chem. 61: 2724–2730 (1989).

C2. Chace, D. H. and Abramson, F. P., Isotope dilution studies: determination of carbon 13, nitrogen 15, and deuterium enriched compounds using capillary gas chromatography-chemical reaction interface/mass spectrometry (GC-CRIMS). Biomed. Environ. Mass Spectrom. 19: 117–122 (1990).

C3. Chace, D. H. and Abramson, F. P. Detection of carbon-14 eluting from a capillary gas chromatograph using CRIMS (chemical reaction interface/mass spectrometry). J. Chromatogr. 527: 1–10 (1990).

C4. Chace, D. H. and Abramson, F. P. Selective detection of stable isotope-labeled drugs and metabolites using capillary gas chromatography-reaction interface/mass spectrometry. in: T. A. Baillie and J. R. Jones (Editors), Synthesis and Applications of Isotopically Labelled Compounds. Proceedings of the Third International Symposium, Innsbruck, Austria, 1988, Elsevier, Amsterdam, 1989, 253–258.

C5. Chu, C., Liu, B., Watson, D., Szu, S., Bryla, D., Shiloach, J., Schneerson, R., and Robbins, J. B., Preparation, characterization, and Immunogenicity of conjugates composed of the O-specific polysaccharide of Shigella dysenteriae Type 1 (Shiga's Bacillus) bound to tetanus toxoid. Infection Immun. 59: 4450–4458 (1991).

F1. Freedman, P. A., Gillyon, E. C. P., and Jumeau, E. J., Design and application of a new instrument for GC-isotope ratio MS. Amer. Laboratory, 114–119, June 1988.

G1. Gersovitz, M.; Bier, D.; Matthews, D.; Udall, J.; Munro, H.; Young, V. R. *Metabolism* 1980, 29, 1087–1094.

G2. Goodman, K. J.; Brenna, J. T. Anal. Chem. 1992, 64, 1088–1095.

H1. Hachey, D. L., Wong, W. W., Boutton, T. W., and Klein, P. D., Isotope ratio measurements in nutrition and biomedical research. Mass Spectrom. Rev. 6: 289–328 (1987).

H2. Hag Ali, M., Abramson, F. P., Fetterolf, D. D., and Cohn, V. H. Metabolism studies of the antischistosomal drug praziquantel using tandem mass spectrometry: Distribution of parent drug and ten metabolites obtained from control and schistosome-infected mouse urine. Biomed. Environ. Mass Spectrom. 19: 186–190 (1990).

H3. Hayes, J. M., Freeman, K. H., Ricci, M. P., Studley, S. A., Merritt, D. A., Brzuzy, L., Brand, W. A., and Habfast, K. Isotope-ratio-monitoring gas chromatography mass spectrometry. Proc. 37th ASMS Conference. 33–34 (1989).

H4. Heck, H. d'A.; McReynolds, J. H.; Anbar, M. (1977) *Cell Tissue Kinet.* 1977, 10, 111–119.

J1. Javitt, N. B. FASEB J. 1990 4, 161–168.

K1. Kennedy, B. V.; Krouse, H. R. Can. *J. Physiol. Pharmacol.* 1990, 68, 960–972.

L1. Lapidot, A.; Nissim, I. (1980) *Metabolism* 1980, 29, 230–239.

L2. Lehninger, A. L. *Biochemistry*, 2nd Ed.; Worth Publishers: New York, 1978; Chapter 26 and page 165.

M1. Markey, S. P. and Abramson, F. P., Capillary gas chromatography/mass spectrometry with a microwave discharge interface for determination of radioactive-carbon-containing compounds. Anal. Chem. 54: 2375–2376 (1982).

M2. Markey, S. P. and Abramson, F. P., Element and isotope specific detection by capillary gas chromatography-mass spectrometry using a microwave discharge interface; in: W. P. Duncan and A. B. Susan (Eds.), Synthesis and Applications of Isotopically Labeled Compounds. Proceedings of an International Symposium, Kansas City, Mo., U.S.A., 1982, Elsevier, Amsterdam; 291–296, 1983.

M3. Matthews, D. E., and Hayes, J. M., Isotope-ratio-monitoring gas chromatography-mass spectrometry. Anal. Chem. 50: 1465–1473 (1978).

M4. Moini, M, Chace, D. H., and Abramson, F. P., Selective detection of sulfur-containing compounds by gas chromatography/chemical reaction interface mass spectrometry. J. Am. Soc. Mass Spectrom. 2: 250–255 (1991).

M5. Moini, M. and Abramson, F. P., A moving belt device to couple HPLC and CRIMS (chemical reaction interface/mass spectrometry). Biol. Mass Spectrom. 20: 308–312 (1991).

M6. Motulski, H. J.: Ransnas, L. A. *FASEB J.* 1987, 1, 365–374.

M7. Macallan, D. C., Fullerton, C. A., Neese, R., Haddock, K., Park, S., Hellerstein, M. K. Proc. Nat. Acad. Sci. 1998, 95, 708–713.

N1. Nakagawa, A., Kitagawa, A., Nakamura, K., Schoeller, D. A., Slater, R., Minagawa, M., and Kaplan, I. R., Evaluation of isotope ratio (IR) mass spectrometry for the study of drug metabolism. Biomed. Environ. Mass Spectrom. 12: 502–506 (1985).

O1. Ormerod, M. G. *Flow Cytometry: A Practical Approach*, 2nd ed.; Oxford University Press Inc.: New York, 1994; p. 165.

P1. Patterson, B. W., Hachey, D. L., Cook, G. L., Amann, J. M., and Klein, P. D., Incorporation of a stable isotopically labeled amino acid into multiple human lipoproteins. J. Lipid Res. 32: 1963–1072 (1991).

P2. Preston, T., and Owens, N. J. P., Preliminary 13C measurements using a gas chromatograph interfaced to an isotope ratio mass spectrometer. Biomed. Environ. Mass Spectrom. 12: 510–513 (1985).

P3. Preston, T., and McMillan, D. C., Rapid sample throughput for biomedical stable isotope tracer studies. Biomed. Environ. Mass Spectrom. 16: 229–235 (1988).

S1. Sano, M, Yotsui, Y., Abe, H., and Sasaki, S., A new technique for the detection of metabolites labelled by the isotope 13C using mass fragmentography. Biomed. Mass Spectrom. 3: 1–3 (1976).

S2. Saris, C. P.; Damman, S. J.; van den Ende, A. M. C.; Westra, J. G.; den Engels, L. A. *Carcinogenesis* 1995, 16, 1543–1548.

S3. Silfer, J. A., Engel, M. H., Macko, S. A., and Jumeau, E. J., Stable carbon isotope analysis of amino acid enantiomers by conventional isotope ratio mass spectrometry and combined gas chromatography/isotope ratio mass spectrometry. Anal. Chem. 63: 370–374 (1991).

S4. Strong, J. M.; Anderson, L. W.; Monks, A.; Chisena, C. A.; Cysyk, R. L. (1983) *Anal. Biochem.* 1983, 132, 243–253.

S5. Sugino, N., Arai, J., Akimoto, M., Miwa, T., and Takuma, T., Stable isotope 15N-urea and clinical research in nephrology. Japan. J. Nephrol. 32: 849–853 (1990).

T1. Teffera, Y.; Kusmierz, J. J.; Abramson, F. P. *Anal. Chem.* 1996, 68: 1888–1894.

V1. Vestal, M. L., Winn, D., Vestal, C. H., and Wilkes, J. G., Application of combination ion source to detect environmentally important compounds. in: M. A. Brown, Ed., "Liquid Chromatography/Mass Spectrometry", ACS Symposium Series 420, Am. Chem. Soc., Washington DC (1990), pp. 215–231.

W1. Walser, M. Use of isotopic urea to study distribution and degradation of urea in man. B. Schmidt-Nielsen Ed., "Urea and the Kidney", Int. Cong. Ser. 195: 421–429 (1970).

W2. Wolfe, R. R. *Radioactive and Stable Isotope Tracers in Biomedicine: Principles and Practice of Kinetic Analysis*, Wiley-Liss, Inc.: New York, 1992.

Z1. Zaharevitz, D. W.; Anderson, L. W.; Strong, J. M.; Hyman, R.; Cysyk, R. L. (1990) *Eur. J. Biochem.* 1990, 187, 437–440.

The purpose of the above description and examples is to illustrate some embodiments of the present invention without implying any limitation. It is apparent to those of skill in the art that various modifications and variations may be made to the composition and method of the present invention without departing from the spirit or scope of the invention. All patents and publications cited herein are incorporated by reference in their entireties.

I claim:

1. A method of measuring enrichment of a stable isotope in DNA isolated from a sample containing replicating DNA that has been exposed to a stable-isotope-labeled DNA precursor, the method comprising the steps of:
   (a) providing a DNA precursor labeled with a stable isotope,
   (b) adding the stable-isotope-labeled DNA precursor to a sample that contains replicating DNA whereby the stable-isotope-labeled DNA precursor is incorporated by way of de novo purine or pyrimidine biosynthesis or by biochemical metabolic salvage pathways into new strands of the replicating DNA,
   (c) isolating a portion of DNA from the sample containing the replicating DNA;
   (d) decomposing and reformulating the isolated portion of DNA from step (c) to form gaseous species capable of being measured with an isotope ratio mass spectrometer; and
   (e) detecting the stable isotope in the gaseous species with an isotope ratio mass spectrometer whereby an isotope ratio is determined, wherein enrichment of the stable isotope in the isolated portion of DNA is determined by comparison of the determined isotope ratio with a baseline.

2. A method of measuring the enrichment of a stable isotope of any one of hydrogen, carbon, oxygen and nitrogen in DNA isolated from a sample containing replicating DNA, the method comprising the steps of:
   (a) providing a DNA precursor labeled with a stable isotope of any one of hydrogen, carbon, oxygen and nitrogen,
   (b) add ing the stable-isotope-labeled DNA precursor to a sample that contains replicating DNA whereby the stable-isotope-labeled DNA precursor is incorporated by way of de novo purine or pyrimidine biosynthesis or by biochemical metabolic salvage pathways into new strands of the replicating DNA,
   (c) isolating a portion of DNA from the sample containing the replicating DNA;
   (d) measuring the enrichment of the stable isotope in the portion of DNA from step (c) with a chemical reaction interface mass spectrometer or an isotope ratio mass spectrometer, wherein the step of measuring with a chemical reaction interface mass spectrometer or an isotope ratio mass spectrometer is carried out by decomposing and reformulating the portion of DNA from step (c) to form gaseous species capable of being measured with a chemical reaction interface mass spectrometer or an isotope ratio mass spectrometer, detecting the stable isotope in the gaseous species with a chemical reaction interface mass spectrometer or an isotope ratio mass spectrometer and comparing a detected amount of the stable isotope with a baseline or control.

3. A method of measuring enrichment of a stable isotope in DNA isolated from a sample containing replicating DNA that has been exposed to a stable-isotope-labeled DNA precursor, the method comprising the steps of:
   (a) providing a DNA precursor labeled with a stable isotope,
   (b) adding the stable-isotope-labeled DNA precursor to a sample that contains replicating DNA whereby the stable-isotope-labeled DNA precursor is incorporated by way of de novo purine or pyrimidine biosynthesis or by biochemical metabolic salvage pathways into new strands of the replicating DNA,
   (c) isolating or purifying a portion of DNA from the sample containing the replicating DNA;
   (d) decomposing and reformulating the isolated or purified DNA of step (c) to produce a stable-isotope-labeled gaseous species on which an enrichment measurement is made;
   (e) measuring the amount of the stable isotope in the gaseous species with a mass spectrometer, and determining the enrichment of the stable isotope by comparing the measured amount of the stable isotope with a baseline or control.

4. The method of claim 3 wherein said stable isotope is a stable isotope of hydrogen, oxygen, carbon or nitrogen.

5. The method of claim 3 wherein said labeled precursor is selected from the group consisting of glycine, adenosine, cytosine, guanine and thymine.

6. The method of claim 3 wherein said spectrometer is a chemical reaction interface mass spectrometer or an isotope ratio mass spectrometer.

7. The method of claim 3 wherein said decomposing and reformulating step is performed by a copper oxide furnace.

8. A method of measuring enrichment of a stable isotope in DNA isolated from a sample containing replicating DNA that has been exposed to a stable-isotope-labeled DNA precursor, the method comprising the steps of:
   (a) providing a DNA precursor labeled with a stable isotope,
   (b) adding the stable-isotope-labeled DNA precursor to a sample that contains replicating DNA whereby the stable-isotope-labeled DNA precursor is incorporated by way of de novo purine or pyrimidine biosynthesis or by biochemical metabolic salvage pathways into new strands of the replicating DNA,
   (c) isolating or purifying a portion of DNA from the sample containing the replicating DNA;
   (d) optionally degrading the DNA of step (c);
   (e) analyzing the DNA obtained in steps (c) or (d) by chromatography;
   (f) decomposing and reformulating analyzed DNA from step (e) to form gaseous species capable of being measured with a mass spectrometer; and (g) measuring the amount of the stable isotope in the gaseous species with a mass spectrometer, and determining the enrichment of the stable isotope by comparing the measured amount of the stable isotope with a baseline or control.

9. The method of claim 8 wherein said chromatography is high performance liquid chromatography, gas chromatography or capillary electrophoresis.

10. A method of measuring enrichment of a stable isotope in DNA isolated from a sample containing replicating DNA that has been exposed to a stable-isotope-labeled DNA precursor, the method comprising the steps of:

(a) providing a DNA precursor labeled with a stable isotope, wherein the stable-isotope-labeled DNA precursor is selected so that the stable isotope can become incorporated into at least one of the four DNA bases, but is not incorporated into all four DNA bases, (b) adding the stable-isotope-labeled DNA precursor to a sample that contains replicating DNA whereby the stable-isotope-labeled DNA precursor is incorporated by way of de novo purine or pyrimidine biosynthesis or by biochemical metabolic salvage pathways into new strands of the replicating DNA, (c) isolating or purifying a portion of DNA from the sample containing the replicating DNA;

(d) degrading the DNA of step (c) into a set of different DNA base components wherein at least one DNA base component is a type into which the stable isotope could be incorporated in step (b) and wherein at least one DNA base component is not a type into which the stable isotope could be incorporated in step (b);

(e) analyzing the degraded DNA of step (d) by high performance liquid chromatography, whereby the DNA base components are separated, (f) measuring amounts of stable isotope label in each DNA base component by chemical reaction interface mass spectroscopy (CRIMS) or isotope ratio mass spectroscopy, wherein at least one DNA base component that is not a type into which the stable isotope could be incorporated in step (b) serves as an internal standard for determining the enrichment of the stable isotope in the DNA.

11. The method of claim 10, wherein the stable-isotope-labeled DNA precursor is any one of cytosine, adenosine, thymine, and guanine.

12. A method of measuring the proliferation of a cell type in a patient who has received chemotherapy, the method comprising the steps of (a) providing a DNA precursor labeled with a stable isotope, wherein the stable-isotope-labeled DNA precursor is selected so that the stable isotope can become incorporated into at least one of the four DNA bases, but is not incorporated into all four DNA bases, (b) administering the stable-isotope-labeled DNA precursor to a patient who has received chemotherapy, whereby the stable-isotope-labeled DNA precursor is incorporated by way of de novo purine or pyrimidine biosynthesis or by biochemical metabolic salvage pathways into new strands of replicating DNA in dividing cells of the patient, (c) thereafter, obtaining a sample from the patient, the sample containing cells of the cell type to be measured for proliferation, (d) isolating or purifying DNA from the cells of the cell type to be measured for proliferation;

(e) degrading the DNA of step (d) into a set of different DNA base components wherein at least one DNA base component is a type into which the stable isotope could be incorporated in step (b) and wherein at least one DNA base component is not a type into which the stable isotope could be incorporated in step (b);

(f) analyzing the degraded DNA of step (e) by high performance liquid chromatography, whereby the DNA base components are separated, (g) measuring amounts of stable isotope in each DNA base component by chemical reaction interface mass spectroscopy (CRIMS) or isotope ratio mass spectroscopy, wherein at least one DNA base component that is not a type into which the stable isotope could be incorporated in step (b) serves as an internal standard for determining the enrichment of the stable isotope in the DNA, and (h) comparing the enrichment of the stable isotope in the DNA from the cells of the cell type to be measured for proliferation with a baseline or standard to determine the proliferation of the cell type.

13. The method of claim 12 wherein the cell type is a white blood cell or a subpopulation thereof and wherein the method of measuring the proliferation of the cell type is carried out to measure stem-cell reserve.

14. A method of measuring cell proliferation in a patient in response to aging, the method comprising the steps of (a) providing a DNA precursor labeled with a stable isotope, wherein the stable-isotope-labeled DNA precursor is selected so that the stable isotope can become incorporated into at least one of the four DNA bases, but is not incorporated into all four DNA bases, (b) administering the stable-isotope-labeled DNA precursor to a patient to be examined for effects of aging, whereby the stable-isotope-labeled DNA precursor is incorporated by way of de novo purine or pyrimidine biosynthesis or by biochemical metabolic salvage pathways into new strands of replicating DNA in dividing cells of the patient, (c) thereafter, obtaining a sample of cells from the patient, (d) isolating or purifying DNA from the cells;

(e) degrading the DNA of step (d) into a set of different DNA base components wherein at least one DNA base component is a type into which the stable isotope could be incorporated in step (b) and wherein at least one DNA base component is not a type into which the stable isotope could be incorporated in step (b);

(f) analyzing the degraded DNA of step (e) by high performance liquid chromatography, whereby the DNA base components are separated, (g) measuring amounts of stable isotope in each DNA base component by chemical reaction interface mass spectroscopy (CRIMS) or isotope ratio mass spectroscopy, wherein at least one DNA base component that is not a type into which the stable isotope could be incorporated in step (b) serves as an internal standard for determining the enrichment of the stable isotope in the DNA, and (h) comparing the enrichment of the stable isotope in the DNA from the cells with a baseline or standard to determine the proliferation of the cells of the patient.

15. A method of measuring lymphocyte proliferation in a patient, the method comprising the steps of (a) providing a DNA precursor labeled with a stable isotope, wherein the stable-isotope-labeled DNA precursor is selected so that the stable isotope can become incorporated into at least one of the four DNA bases, but is not incorporated into all four DNA bases, (b) administering the stable-isotope-labeled DNA precursor to a patient to be examined for lymphocyte proliferation, whereby the stable-isotope-labeled DNA precursor is incorporated by way of de novo purine or pyrimidine biosynthesis or by biochemical metabolic salvage pathways into new strands of replicating DNA in dividing cells of the patient, (c) thereafter, obtaining a sample of lymphocytes from the patient, (d) isolating or purifying DNA from the lymphocytes;

(e) degrading the DNA of step (d) into a set of different DNA base components wherein at least one DNA base component is a type into which the stable isotope could be incorporated in step (b) and wherein at least one DNA base component is not a type into which the stable isotope could be incorporated in step (b);

(f) analyzing the degraded DNA of step (e) by high performance liquid chromatography, whereby the DNA base components are separated, (g) measuring amounts of stable isotope in each DNA base component by chemical reaction interface mass spectroscopy (CRIMS) or isotope ratio mass spectroscopy, wherein at least one DNA base component that is not a type into which the stable isotope could be incorporated in step (b) serves as an internal standard for determining the enrichment of the stable isotope in the DNA; and (h) comparing the enrichment of the stable isotope in the DNA from the lymphocytes with a baseline or standard to determine the proliferation of lymphocytes of the patient.

16. The method of claim 14 wherein the patient is a transplant patient.

17. The method of claim 14 wherein the method is carried out on a patient with drug hypersensitivities.

18. A method of measuring enrichment of $^{13}$C in DNA isolated from a sample containing replicating DNA that has been exposed to a $^{13}$C-labeled glycine, the method comprising the steps of:

(a) providing $^{13}$C-labeled glycine, (b) adding the $^{13}$C-labeled glycine to a sample that contains replicating DNA whereby the $^{13}$C-labeled glycine is incorporated by way of de novo purine biosynthesis into new strands of the replicating DNA, (c) isolating or purifying a portion of DNA from the sample containing the replicating DNA;

(d) degrading the DNA of step (c) into a set of different DNA base components wherein at least one DNA base component is a type into which $^{13}$C could be incorporated in step (b) and wherein at least one DNA base component is not a type into which $^{13}$C could be incorporated in step (b);

(e) analyzing the degraded DNA of step (d) by high performance liquid chromatography, whereby the DNA base components are separated, (f) measuring amounts of $^{13}$C in each DNA base component by chemical reaction interface mass spectroscopy (CRIMS) or isotope ratio mass spectroscopy, wherein at least one DNA base component that is not a type into which $^{13}$C could be incorporated in step (b) serves as an internal standard for determining the enrichment of $^{13}$C in the DNA.

* * * * *

UNITED STATES PATENT AND TRADEMARK OFFICE
CERTIFICATE OF CORRECTION

PATENT NO.      : 6,355,416 B1                                                      Page 1 of 1
DATED           : March 12, 2002
INVENTOR(S)     : Abramson, Fred P.

It is certified that error appears in the above-identified patent and that said Letters Patent is hereby corrected as shown below:

Column 1,
Line 8, please add the following:
            -- STATEMENT AS TO FEDERALLY SPONSORED RESEARCH
Work described herein was supported by NSF grant BIR9216935. The U.S. Government has certain rights in the invention. --

Signed and Sealed this

Twenty-eighth Day of October, 2003

JAMES E. ROGAN
*Director of the United States Patent and Trademark Office*